United States Patent [19]
Yoon et al.

[11] Patent Number: 5,922,871
[45] Date of Patent: Jul. 13, 1999

[54] TEREPHTHALAMIDE DERIVATIVES

[75] Inventors: Sung Joon Yoon, Seoul; Yong Ho Chung, Kyungki-do; Sang Wook Lee, Kyungki-do; Hyeong Su Sim, Kyungki-do; Yong Kyun Park, Kyungki-do; Jong Woo Kim, Kyungki-do; Yong Huh, Kyungki-do; Jae In Yoon, Kyungki-do; Sang Jin Park, Seoul, all of Rep. of Korea

[73] Assignee: Dongwha Pharmaceutical Ind. Co., Ltd., Seoul, Rep. of Korea

[21] Appl. No.: 08/956,948

[22] Filed: Oct. 23, 1997

[30] Foreign Application Priority Data

May 27, 1997 [KP] DPR of Korea ............... 97-20957
May 27, 1997 [KP] DPR of Korea ............... 97-20958
Jun. 5, 1997 [KP] DPR of Korea ............... 97-23289
Jul. 31, 1997 [KP] DPR of Korea ............... 97-36589

[51] Int. Cl.$^6$ ............... C07D 413/00; C07D 401/00; A61K 31/495
[52] U.S. Cl. ............... 544/360; 544/364; 544/336; 544/358; 544/359; 514/255
[58] Field of Search ............... 544/364, 360; 514/255

[56] References Cited

U.S. PATENT DOCUMENTS 5,489,593 2/1996 Palmer et al. ............... 514/252
5,563,142 10/1996 Palmer et al. ............... 514/253
5,599,930 2/1997 Romero et al. ............... 544/121

FOREIGN PATENT DOCUMENTS 0563732 10/1993 European Pat. Off. .
0563734 10/1993 European Pat. Off. .

OTHER PUBLICATIONS

Romero, D.L., "Nonnucleoside reverse transcriptase inhibitors that potently and specifically block human immunodeficiency virus type 1 replication," *Proc. Natl. Acad. Sci. USA*, vol. 88, pp. 8806–8810, Oct. 1991.

Beach, et al., "Synthesis of Enantiomerically Pure (2'R, 5'S)-(-)-1-[2-(Hydroxymethyl)oxathiolan-5-yl]cytosine as a Potent Antiviral Agent Against Hepatitis B Virus (HBV) and Human Immunodeficiency Virus (HIV)," *Journal of Organic Chemistry,*, vol. 57, No. 8 (1992), pp. 2217–2219.

Romero, et al., "Discovery, Synthesis, and Bioactivity of Bis(Heteroaryl)Piperazines. 1. A Novel Class of Non–Nucleoside HIV–1 Reverse Transcriptase Inhibitors," *Journal of Medicinal Chemistry*, vol. 37, No. 7 (1994), pp. 999–1014.

*Primary Examiner*—José G. Dees
*Assistant Examiner*—Sabiha N. Qazi
*Attorney, Agent, or Firm*—Finnegan, Henderson, Farabow, Garrett & Dunner, L.L.P.

[57] ABSTRACT

The present invention relates to novel terephthalamide derivatives and in particular to novel terephthalamide derivatives of the following formula 1, its pharmaceutically acceptable salts as antiviral agents having remarkable inhibitory actions against the proliferation of various viruses including HIV and HBV, and preparing method thereof

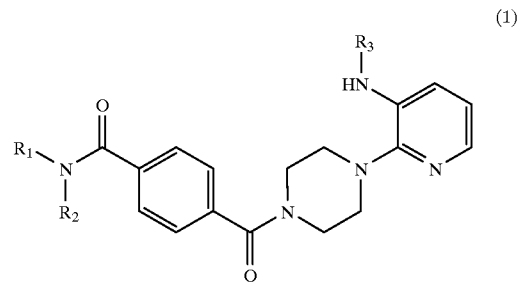

(1)

wherein $R_1$, $R_2$ and $R_3$ are the same as defined in the detailed description of the present invention.

15 Claims, No Drawings

TEREPHTHALAMIDE DERIVATIVES

BACKGROUND OF THE INVENTION

1. Field of the Invention

The present invention relates to novel terephthalamide derivatives and in particular to novel terephthalamide derivatives of the following formula 1, its pharmaceutically acceptable salts as antiviral agents having remarkable inhibitory activities against the proliferation of various viruses including HIV and HBV, and preparing method thereof.

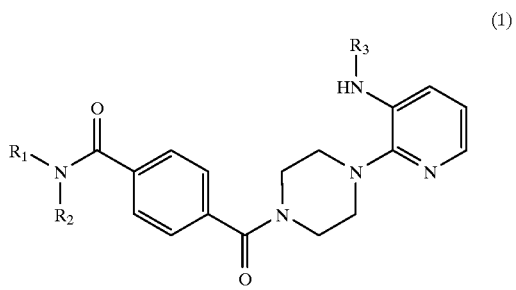

(1)

Wherein:
- $R_1$ and $R_2$ represent independently one selected from hydrogen atom; phenyl group; benzyl group; $C_1$~$C_6$ alkyl group; substituted $C_1$~$C_4$ alkyl group in which substituent selected from di($C_1$~$C_4$ alkyl)amino, acetylamino group and heterocycles; $C_1$~$C_5$ hydroxyalkyl group; substituted $C_1$~$C_4$ hydroxyalkyl group in which one or two suitable substituents selected from phenyl, benzyl, $C_1$~$C_4$ hydroxyalkyl and $C_1$~$C_7$ alkyl group; $C_2$~$C_6$ alkoxyalkyl group; di($C_2$~$C_6$ alkoxy)alkyl group; $C_2$~$C_5$ (hydroxyalkoxy)alkyl group; with the proviso that $R_1$ and $R_2$ do not simultaneously represent hydrogen atom; in case where either $R_1$ or $R_2$ is hydrogen atom, the stereospecificity of (R)- or (S)-type may be represented;
- further, $R_1$ and $R_2$ may be combined with one or two hetero atoms selected from nitrogen, oxygen and sulfur to form five or six membered heterocycles, wherein the heterocycles may be substituted with one substituent selected from $C_1$~$C_5$ alkyl, $C_3$~$C_6$ cycloalkyl, $C_3$~$C_5$ (hydroxyalkoxy)alkyl, $C_2$~$C_5$ hydroxyalkyl, $C_1$~$C_3$ alkyl-substituted $C_1$~$C_4$ hydroxyalkyl, $C_1$~$C_4$ dihydroxyalkyl and $C_1$~$C_3$ alkyl-substituted $C_1$~$C_4$ dihydroxyalkyl group;
- $R_3$ represents $C_1$~$C_4$ alkyl group;
- further, the above mentioned alkyl group includes straight or branched alkyl group or cycloalkyl group.

2. Description of the Prior Art

Worldwide, about 300 million people are infected with hepatitis B virus(hereinafter referred to as "HBV"), one of the main viruses causing hepatitis and prolonged infection has been associated with cirrhosis and hepatocellular carcinoma. Hitherto, many researcher have focused on the HBV relationship with liver diseases and its molecular-biological characteristics. Some vaccines have been developed to prevent infection but no effective therapy exists for treating hepatitis B infection.

In the past years, it was reported that some nucleoside compounds, which have been mainly developed as an anti-AIDS(Acquired Immune Deficiency Syndrome) agent, are effective HBV inhibitors [*J. Org. Chem.*, 1992, Vol. 57, 2217]. However, these nucleoside compounds as effective drugs against viral hepatitis B have proven to be undesirable due to high costs of drugs, adverse reactions and toxic effects.

Under such circumstances, there is urgent need for the development of hepatitis B drug having remarkable antiviral activities against HBV as a non-nucleoside compound. Recently, quinolones [European unexamined patent No. 563732 and No. 563734] and iridoids [Korean unexamined patent No. 94-1886] have been reported to have anti HBV activity but no significant development progress has been noticeable.

To overcome the side effects and toxicities of the conventional drugs and develop some effective non-nucleoside compounds having remarkable antiviral activities against HBV, the inventor et al. have carried out intensive studies. As a result, the inventors have completed this invention wherein terephthalamide derivatives of non-nucleoside compounds with specific structure of the above formula 1 have been found to have potent inhibitory activities against the proliferation of HBV including human immunodeficiency virus(hereinafter referred to as "HIV") and other viruses.

For example, HBV is a virus different from HIV but during proliferation, they have common replication courses, i.e., a reverse transcription step and the resulting RNA template of RNA-DNA hybrid is degraded. Since terephthalamide derivatives according to the present invention of the formula 1, have mechanism to inhibit such proliferation course, it may be developed as effective inhibitor against the proliferation of various viruses including HBV and HIV.

SUMMARY OF THE INVENTION

Therefore, an object of the present invention is to provide novel terephthalamide derivatives of the following formula 1, its pharmaceutically acceptable salts as antiviral agents having remarkable inhibitory activities against the proliferation of various viruses including HIV and HBV, and preparing method thereof.

DETAILED DESCRIPTION OF THE INVENTION

The present invention is related to novel terephthalamide derivatives of the following formula 1 and its pharmaceutically acceptable salts.

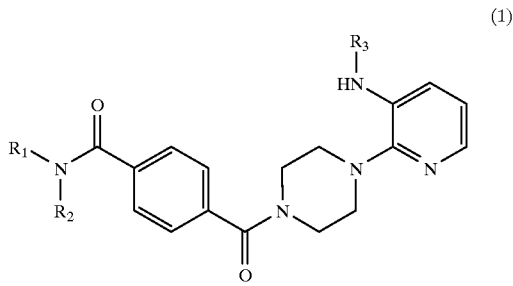

(1)

Wherein: $R_1$, $R_2$ and $R_3$ are the same as defined above, respectively.

The preferred terephthalamide derivatives of the formula 1 according to the present invention, are as follows:

In case where from the above $R_1$ and $R_2$, one is hydrogen atom and the other is an $C_1$~$C_3$ alkoxy $C_1$~$C_4$ alkyl group; di($C_2$~$C_5$ alkoxy) $C_1$~$C_4$ alkyl group; 1,3-dioxolan-2-yl-methyl group; tetrahydrofuran-2-yl-methyl group; 2-(morpholin-4-yl)ethyl group; 3-(morpholin-4-yl)propyl group; 2-(piperidin-1-yl) ethyl group; di($C_1$~$C_3$ alkyl) amino $C_1$~$C_3$ alkyl group; 2-(acetylamino)ethyl group; 2-hydroxyethyl group; or substituted 2-hydroxyethyl group with one or two suitable substituents selected from phenyl group, benzyl group, $C_1$~$C_3$ hydroxyalkyl group and $C_1$~$C_5$ alkyl group, In case where from the above $R_1$ and $R_2$, one is $C_1$~$C_3$ alkyl group and the other is di($C_1$~$C_3$ alkoxy) $C_2$~$C_3$ alkyl group; 1,3-dioxolan-2-yl-methyl group; tetrahydrofuran-2-yl-methyl group; 2-(morpholin-4-yl)ethyl group; 3-(morpholin-4-yl)propyl group; 2-(piperidin-1-yl)ethyl group; 2-hydroxyethyl group; di($C_1$~$C_3$ alkyl)amino $C_1$~$C_3$ alkyl group; or 2-(acetylamino)ethyl group, In case where the above $R_1$ and $R_2$ are simultaneously $C_1$~$C_3$ alkyl group, hydroxyethyl group or 2-hydroxypropyl group, and In case where the above $R_1$ and $R_2$ are combined with one or two hetero atoms selected from nitrogen, oxygen and sulfur to form heterocycles such as morpholine, thiomorpholine, pyrrolidine, piperidine or piperazine ring, in particularly in the case of piperazine ring it is selectively substituted with hydrogen atom, $C_1$~$C_5$ alkyl group, $C_3$~$C_6$ cycloalkyl group, $C_2$~$C_5$ hydroxyalkyl group, $C_2$~$C_4$ dihydroxyalkyl group, $C_3$~$C_5$ (hydroxyalkoxy)alkyl group, $C_1$~$C_3$ alkyl-substituted $C_1$~$C_4$ hydroxyalkyl group, (2R)-3-hydroxy-2-methylpropyl group or (2S)-3-hydroxy-2-methylpropyl group.

The more preferred terephthalamide derivatives of the formula 1 according to the present invention, are as follows:

In case where $R_1$ is 2-hydroxyethyl group, while $R_2$ is hydrogen atom, methyl, ethyl or isopropyl group, In case where $R_1$ and $R_2$ are simultaneously 2-hydroxyethyl, 2-hydroxypropyl, ethyl or isopropyl group, In case where $R_1$ is hydrogen atom, while $R_2$ is a substituted 2-hydroxyethyl group, showing (R)- or (S)-type of stereospecificity, in which a substituent in particular such as methyl, ethyl, isopropyl, phenyl, benzyl or hydroxymethyl group at 1- or 2-position, or substituted 2-hydroxyethyl group in which two substituents in particular such as methyl, ethyl or hydroxymethyl group at 1-position, In case where $R_1$ is hydrogen atom or 2-methoxyethyl group, while $R_2$ is 2-methoxyethyl, 3-methoxypropyl, 3-ethoxypropyl or 3-isopropoxypropyl group, In case where $R_1$ is hydrogen atom or methyl group, while $R_2$ is 2,2-dimethoxyethyl, 2,2-diethoxyethyl, 1,3-dioxolan-2-yl-methyl, tetrahydrofuran-2-yl-methyl, 2-(morpholin-4-yl)ethyl, 3-(morpholin-4-yl)propyl or 2-(piperidin-1-yl)ethyl group, In case where $R_1$ is hydrogen atom, methyl or ethyl group, while $R_2$ is 2-(dimethylamino)ethyl, 2-(diethylamino)ethyl, 3-(dimethylamino)propyl, 3-(diethylamino)propyl or 2-(acetylamino)ethyl group, In case where $R_1$ and $R_2$ are forming heterocycles such as morpholine, thiomorpholine, pyrrolidine, piperidine or piperazine ring, together with nitrogen atom, In case where $R_1$ and $R_2$ are forming a piperazine ring, while the nitrogen atom at 4-position is selectively substituted with methyl, ethyl, isopropyl, cyclopropyl, cyclopentyl, 2-hydroxyethyl, 3-hydroxypropyl, 2,3-dihydroxypropyl, 2,2-dimethyl-3-hydroxypropyl, (2R)-3-hydroxy-2-methylpropyl, (2S)-3-hydroxy-2-methylpropyl or 2-(2-hydroxyethoxy)ethyl group, and In particular preferred terephthalamide derivatives of the formula 1, both $R_1$ and $R_2$ are the same as defined above, while $R_3$ is an isopropyl group.

According to the present invention, the typical examples of terephthalamide derivatives of the above formula 1, are as follows:

1-[N-(2-Hydroxyethyl)carbamoyl]-4-[1-[3-(isopropylamino)-2-pyridyl]piperazin-4-yl-carbonyl]benzene (Compound No. 1), 1-[N-(3-Hydroxypropyl)carbamoyl]-4-[1-[3-(isopropylamino)-2-pyridyl]piperazin-4-yl-carbonyl]benzene (Compound No. 2), 1-[N-(4-Hydroxybutyl)carbamoyl]-4-[1-[3-(isopropylamino)-2-pyridyl]piperazin-4-yl-carbonyl]benzene (Compound No. 3), 1-[N-(5-Hydroxypentyl)carbamoyl]-4-[1-[3-(isopropylamino)-2-pyridyl]piperazin-4-yl-carbonyl]benzene (Compound No. 4), 1-[N-(2-Hydroxyethyl)-N-methylcarbamoyl]-4-[1-[3-(isopropylamino)-2-pyridyl]piperazin-4-yl-carbonyl]benzene (Compound No. 5), 1-[N-Ethyl-N-(2-hydroxyethyl)carbamoyl]-4-[1-[3-(isopropylamino)-2-pyridyl]piperazin-4-yl-carbonyl]benzene (Compound No. 6), 1-[N-(2-Hydroxyethyl)-N-propylcarbamoyl]-4-[1-[3-(isopropylamino)-2-pyridyl]piperazin-4-yl-carbonyl]benzene (Compound No. 7), 1-[N-(2-Hydroxyethyl)-N-(1-methylethyl)carbamoyl]-4-[1-[3-(isopropylamino)-2-pyridyl]piperazin-4-yl-carbonyl]benzene (Compound No. 8), 1-[N-Butyl-N-(2-hydroxyethyl)carbamoyl]-4-[1-[3-(isopropylamino)-2-pyridyl]piperazin-4-yl-carbonyl]benzene (Compound No. 9), 1-[N-Benzyl-N-(2-hydroxyethyl)carbamoyl]-4-[1-[3-(isopropylamino)-2-pyridyl]piperazin-4-yl-carbonyl]benzene (Compound No. 10), 1-[N-(2-Hydroxyethyl)-N-phenylcarbamoyl]-4-[1-[3-(isopropylamino)-2-pyridyl]piperazin-4-yl-carbonyl]benzene (Compound No. 11), 1-[N,N-Bis(2-hydroxyethyl)carbamoyl]-4-[1-[3-(isopropylamino)-2-pyridyl]piperazin-4-yl-carbonyl]benzene (Compound No. 12), 1-[N,N-Diethylcarbamoyl]-4-[1-[3-(isopropylamino)-2-pyridyl]piperazin-4-yl-carbonyl]benzene (Compound No. 13), 1-[N,N-Bis(1-methylethyl)carbamoyl]-4-[1-[3-(isopropylamino)-2-pyridyl]piperazin-4-yl-carbonyl]benzene (Compound No. 14), 4-[1-[3-(Isopropylamino)-2-pyridyl]piperazin-4-yl-carbonyl]-1-(N-methyl-N-propylcarbamoyl)benzene (Compound No. 15), 1-[N,N-Bis(2-hydroxypropyl)carbamoyl]-4-[1-[3-(isopropylamino)-2-pyridyl]piperazin-4-yl-carbonyl]benzene (Compound No. 16), 1-[N-[2-(2-Hydroxyethoxy)ethyl]carbamoyl]-4-[1-[3-(isopropylamino)-2-pyridyl]piperazin-4-yl-carbonyl]benzene (Compound No. 17), 1-[N-Ethyl-N-(2-hydroxyethyl)carbamoyl]-4-[1-[3-(ethylamino)-2-pyridyl]piperazin-4-yl-carbonyl]benzene (Compound No. 18), 1-[4-[1-[3-(Isopropylamino)-2-pyridyl]piperazin-4-yl-carbonyl]benzoyl]piperazine (Compound No. 19), 1-[4-[1-[3-(Isopropylamino)-2-pyridyl]piperazin-4-yl-carbonyl]benzoyl]-4-methylpiperazine (Compound No. 20), 4-Ethyl-1-[4-[1-[3-(isopropylamino)-2-pyridyl]piperazin-4-yl-arbonyl]benzoyl]piperazine (Compound No. 21), 4-Cyclopentyl-1-[4-[1-[3-(isopropylamino)-2-pyridyl]
piperazin-4-yl-carbonyl]benzoyl]piperazine
(Compound No. 22), 1-[4-[1-[3-(Isopropylamino)-2-pyridyl]piperazin-4-yl-
carbonyl]benzoyl]-4-propylpiperazine (Compound No.
23), 1-[4-[1-[3-(Isopropylamino)-2-pyridyl]piperazin-4-yl-
carbonyl]benzoyl]-4-(1-methylethyl)piperazine
(Compound No. 24), 4-Cyclopropyl-1-[4-[1-[3-(isopropylamino)-2-pyridyl]
piperazin-4-yl-carbonyl]benzoyl]piperazine
(Compound No. 25), 4-(2-Hydroxyethyl)-1-[4-[1-[3-(isopropylamino)-2-
pyridyl]piperazin-4-yl-carbonyl]benzoyl]piperazine
(Compound No. 26), 4-(3-Hydroxypropyl)-1-[4-[1-[3-(isopropylam-ino)-2-
pyridyl]piperazin-4-yl-carbonyl]benzoyl]piperazine
(Compound No. 27), 4-[(2R)-3-Hydroxy-2-methylpropyl]-1-[4-[1-[3-
(isopropylamino)-2-pyridyl]piperazin-4-yl-carbonyl]
benzoyl]piperazine (Compound No. 28), 4-[(2S)-3-Hydroxy-2-methylpropyl]-1-[4-[1-[3-
(isopropylamino)-2-pyridyl]piperazin-4-yl-carbonyl]
benzoyl]piperazine (Compound No. 29), 4-(2,2-Dimethyl-3-hydroxypropyl)-1-[4-[1-[3-
(isopropylamino)-2-pyridyl]piperazin-4-yl-carbonyl]
benzoyl]piperazine (Compound No. 30), 4-(2,3-Dihydroxypropyl)-1-[4-[1-[3-(isopropylamino)-2-
pyridyl]piperazin-4-yl-carbonyl]benzoyl]piperazine
(Compound No. 31), 4-[2-(2-Hydroxyethoxy)ethyl]-1-[4-[1-[3-
(isopropylamino)-2-pyridyl]piperazin-4-yl-carbonyl]
benzoyl]piperazine (Compound No. 32), 1-[4-[1-[3-(Ethylamino)-2-pyridyl]piperazin-4-yl-
carbonyl]benzoyl]-4-(2-hydroxyethyl)piperazine
(Compound No. 33), 1-[N-(1,1-Dimethyl-2-hydroxyethyl)carbamoyl]-4-[1-[3-
(isopropylamino)-2-pyridyl]piperazin-4-yl-carbonyl]
benzene (Compound No. 34), 1-[N-[(1S)-2-Hydroxy-1-methylethyl]carbamoyl]-4-[1-
[3-(isopropylamino)-2-pyridyl]piperazin-4-yl-
carbonyl]benzene (Compound No. 35), 1-[N-[(1R)-2-Hydroxy-1-methylethyl]carbamoyl]-4-[1-
[3-(isopropylamino)-2-pyridyl]piperazin-4-yl-
carbonyl]benzene (Compound No. 36), 1-[N-(2-Hydroxy-1-methylethyl)carbamoyl]-4-[1-[3-
(isopropylamino)-2-pyridyl]piperazin-4-yl-carbonyl]
benzene (Compound No. 37), 1-[N-[(1S)-2-Hydroxy-1-(1-methylethyl)ethyl]
carbamoyl]-4-[1-[3-(isopropylamino)-2-pyridyl]
piperazin-4-yl-carbonyl]benzene (Compound No. 38), 1-[N-[(1R)-2-Hydroxy-1-(1-methylethyl)ethyl]
carbamoyl]-4-[1-[3-(isopropylamino)-2-pyridyl]
piperazin-4-yl-carbonyl]benzene (Compound No. 39), 1-[N-[2-Hydroxy-1-(1-methylethyl)ethyl]carbamoyl]-4-
[1-[3-(isopropylamino)-2-pyridyl]piperazin-4-yl-
carbonyl]benzene (Compound No. 40), 1-[N-[(1S)-1-Ethyl-2-hydroxyethyl]carbamoyl]-4-[1-[3-
(isopropylamino)-2-pyridyl]piperazin-4-yl-carbonyl]
benzene (Compound No. 41), 1-[N-[(1R)-1-Ethyl-2-hydroxyethyl]carbamoyl]-4-[1-[3-
(isopropylamino)-2-pyridyl]piperazin-4-yl-carbonyl]
benzene (Compound No. 42), 1-[N-(1-Ethyl-2-hydroxyethyl)carbamoyl]-4-[1-[3-
(isopropylamino)-2-pyridyl]piperazin-4-yl-carbonyl]
benzene (Compound No. 43), 1-[N-[(1S)-2-Hydroxy-1-(2-methylpropyl)ethyl]
carbamoyl]-4-[1-[3-(isopropylamino)-2-pyridyl]
piperazin-4-yl-carbonyl]benzene (Compound No. 44), 1-[N-[(1R)-2-Hydroxy-1-(2-methylpropyl)ethyl]
carbamoyl]-4-[1-[3-(isopropylamino)-2-pyridyl]
piperazin-4-yl-carbonyl]benzene (Compound No. 45), 1-[N-[(1S)-2-Hydroxy-1-(1-methylpropyl)ethyl]
carbamoyl]-4-[1-[3-(isopropylamino)-2-pyridyl]
piperazin-4-yl-carbonyl]benzene (Compound No. 46), 1-[N-[(1S)-1-(Cyclohexylmethyl)-2-hydroxyethyl]
carbamoyl]-4-[1-[3-(isopropylamino)-2-pyridyl]
piperazin-4-yl-carbonyl]benzene (Compound No. 47), 1-[N-[(1S)-2-Hydroxy-1-phenylethyl]carbamoyl]-4-[1-
[3-(isopropylamino)-2-pyridyl]piperazin-4-yl-
carbonyl]benzene (Compound No. 48), 1-[N-[(1R)-2-Hydroxy-1-phenylethyl]carbamoyl]-4-[1-
[3-(isopropylamino)-2-pyridyl]piperazin-4-yl-
carbonyl]benzene (Compound No. 49), 1-[N-[(1S)-1-Benzyl-2-hydroxyethyl]carbamoyl]-4-[1-
[3-(isopropylamino)-2-pyridyl]piperazin-4-yl-
carbonyl]benzene (Compound No. 50), 1-[N-[(1R)-1-Benzyl-2-hydroxyethyl]carbamoyl]-4-[1-
[3-(isopropylamino)-2-pyridyl]piperazin-4-yl-
carbonyl]benzene (Compound No. 51), 1-[N-[Bis(hydroxymethyl)methyl]carbamoyl]-4-[1-[3-
(isopropylamino)-2-pyridyl]piperazin-4-yl-carbonyl]
benzene (Compound No. 52), 1-[N-[1,1-Bis(hydroxymethyl)ethyl]carbamoyl]-4-[1-[3-
(isopropylamino)-2-pyridyl]piperazin-4-yl-carbonyl]
benzene (Compound No. 53), 1-[N-[1,1-Bis(hydroxymethyl)propyl]carbamoyl]-4-[1-
[3-(isopropylamino)-2-pyridyl]piperazin-4-yl-
carbonyl]benzene (Compound No. 54), 1-[N-[Tris(hydroxymethyl)methyl]carbamoyl]-4-[1-[3-
(isopropylamino)-2-pyridyl]piperazin-4-yl-carbonyl]
benzene (Compound No. 55), 1-[N-[(2S)-2-Hydroxypropyl]carbamoyl]-4-[1-[3-
(isopropylamino)-2-pyridyl]piperazin-4-yl-carbonyl]
benzene (Compound No. 56), 1-[N-[(2R)-2-Hydroxypropyl]carbamoyl]-4-[1-[3-
(isopropylamino)-2-pyridyl]piperazin-4-yl-carbonyl]
benzene (Compound No. 57), 1-[N-(2-Hydroxypropyl)carbamoyl]-4-[1-[3-
(isopropylamino)-2-pyridyl]piperazin-4-yl-carbonyl]
benzene (Compound No. 58), 1-[N-(2-Hydroxy-2-phenylethyl)carbamoyl]-4-[1-[3-
(isopropylamino)-2-pyridyl]piperazin-4-yl-carbonyl]
benzene (Compound No. 59), 1-[N-(2,3-Dihydroxypropyl)carbamoyl]-4-[1-[3-
(isopropylamino)-2-pyridyl]piperazin-4-yl-carbonyl]
benzene (Compound No. 60), 4-[1-[3-(Isopropylamino)-2-pyridyl]piperazin-4-yl-
carbonyl]-1-[N-(2-methoxyethyl)carbamoyl]benzene
(Compound No. 61), 1-[N,N-Bis(2-methoxyethyl)carbamoyl]-4-[1-[3-
(isopropylamino)-2-pyridyl]piperazin-4-yl-carbonyl]
benzene (Compound No. 62), 4-[1-[3-(Isopropylamino)-2-pyridyl]piperazin-4-yl-
carbonyl]-1-[N-(2-methoxy-1-methylethyl)carbamoyl]
benzene (Compound No. 63), 4-[1-[3-(Isopropylamino)-2-pyridyl]piperazin-4-yl-carbonyl]-1-[N-(3-methoxypropyl)carbamoyl]benzene (Compound No. 64), 1-[N-(3-Ethoxypropyl)carbamoyl]-4-[1-[3-(isopropylamino)-2-pyridyl]piperazin-4-yl-carbonyl]benzene (Compound No. 65), 1-[N-(3-Isopropoxypropyl)carbamoyl]-4-[1-[3-(isopropylamino)-2-pyridyl]piperazin-4-yl-carbonyl]benzene (Compound No. 66), 4-[1-[3-(Isopropylamino)-2-pyridyl]piperazin-4-yl-carbonyl]-1-[N-[3-(vinyloxy)propyl]carbamoyl]benzene (Compound No. 67), 1-[N-(2,2-Dimethoxyethyl)-N-methylcarbamoyl]-4-[1-[3-(isopropylamino)-2-pyridyl]piperazin-4-yl-carbonyl]benzene (Compound No. 68), 1-[N-(2,2-Dimethoxyethyl)carbamoyl]-4-[1-[3-(isopropylamino)-2-pyridyl]piperazin-4-yl-carbonyl]benzene (Compound No. 69), 1-[N-(2,2-Diethoxyethyl)carbamoyl]-4-[1-[3-(isopropylamino)-2-pyridyl]piperazin-4-yl-carbonyl]benzene (Compound No. 70), 1-[N-[(1,3-Dioxolan-2-yl)methyl]-N-methylcarbamoyl]-4-[1-[3-(isopropylamino)-2-pyridyl]piperazin-4-yl-carbonyl]benzene (Compound No. 71), 4-[1-[3-(Isopropylamino)-2-pyridyl]piperazin-4-yl-carbonyl]-1-[N-[(tetrahydrofuran-2-yl)methyl]carbamoyl]benzene (Compound No. 72), 4-[1-[3-(Isopropylamino)-2-pyridyl]piperazin-4-yl-carbonyl]-1-[N-[[(2R)-tetrahydrofuran-2-yl]methyl]carbamoyl]benzene (Compound No. 73), 4-[1-[3-(Isopropylamino)-2-pyridyl]piperazin-4-yl-carbonyl]-1-[N-[[(2S)-tetrahydrofuran-2-yl]methyl]carbamoyl]benzene (Compound No. 74), 1-[N-[(Furan-2-yl)methyl]carbamoyl]-4-[1-[3-(isopropylamino)-2-pyridyl]piperazin-4-yl-carbonyl]benzene (Compound No. 75), 4-[1-[3-(Isopropylamino)-2-pyridyl]piperazin-4-yl-carbonyl]-1-(morpholin-4-yl-carbonyl)benzene (Compound No. 76), 4-[1-[3-(Isopropylamino)-2-pyridyl]piperazin-4-yl-carbonyl]-1-(thiomorpholin-4-yl-carbonyl)benzene (Compound No. 77), 4-[1-[3-(Isopropylamino)-2-pyridyl]piperazin-4-yl-carbonyl]-1-(thiazolidin-3-yl-carbonyl)benzene (Compound No. 78), 4-[1-[3-(Isopropylamino)-2-pyridyl]piperazin-4-yl-carbonyl]-1-[N-[2-(morpholin-4-yl)ethyl]carbamoyl]benzene (Compound No. 79), 4-[1-[3-(Isopropylamino)-2-pyridyl]piperazin-4-yl-carbonyl]-1-[N-[3-(morpholin-4-yl)propyl]carbamoyl]benzene (Compound No. 80), 4-[1-[3-(Isopropylamino)-2-pyridyl]piperazin-4-yl-carbonyl]-1-[N-[2-(piperidin-1-yl)ethyl]carbamoyl]benzene (Compound No. 81), 4-[1-[3-(Isopropylamino)-2-pyridyl]piperazin-4-yl-carbonyl]-1-[N-[2-(pyrrolidin-1-yl)ethyl]carbamoyl]benzene (Compound No. 82), 1-[N-[2-(Dimethylamino)ethyl]carbamoyl]-4-[1-[3-(isopropylamino)-2-pyridyl]piperazin-4-yl-carbonyl]benzene (Compound No. 83), 1-[N-[2-(Dimethylamino)ethyl]-N-methylcarbamoyl]-4-[1-[3-(isopropylamino)-2-pyridyl]piperazin-4-yl-carbonyl]benzene (Compound No. 84), 1-[N-[2-(Dimethylamino)ethyl]-N-ethylcarbamoyl]-4-[1-[3-(isopropylamino)-2-pyridyl]piperazin-4-yl-carbonyl]benzene (Compound No. 85), 1-[N-[2-(Diethylamino)ethyl]carbamoyl]-4-[1-[3-(isopropylamino)-2-pyridyl]piperazin-4-yl-carbonyl]benzene (Compound No. 86), 1-[N-[2-(Diethylamino)ethyl]-N-methylcarbamoyl]-4-[1-[3-(isopropylamino)-2-pyridyl]piperazin-4-yl-carbonyl]benzene (Compound No. 87), 1-[N-[2-(Diethylamino)ethyl]-N-ethylcarbamoyl]-4-[1-[3-(isopropylamino)-2-pyridyl]piperazin-4-yl-carbonyl]benzene (Compound No. 88), 1-[N-[3-(Dimethylamino)propyl]carbamoyl]-4-[1-[3-(isopropylamino)-2-pyridyl]piperazin-4-yl-carbonyl]benzene (Compound No. 89), 1-[N-[3-(Dimethylamino)propyl]-N-methylcarbamoyl]-4-[1-[3-(isopropylamino)-2-pyridyl]piperazin-4-yl-carbonyl]benzene (Compound No. 90), 1-[N-[3-(Diethylamino)propyl]carbamoyl]-4-[1-[3-(isopropylamino)-2-pyridyl]piperazin-4-yl-carbonyl]benzene (Compound No. 91), 1-[N-[2-(Acetylamino)ethyl]carbamoyl]-4-[1-[3-(isopropylamino)-2-pyridyl]piperazin-4-yl-carbonyl]benzene (Compound No. 92), 4-[1-[3-(Isopropylamino)-2-pyridyl]piperazin-4-yl-carbonyl]-1-(piperidin-1-yl-carbonyl)benzene (Compound No. 93), 4-[1-[3-(Isopropylamino)-2-pyridyl]piperazin-4-yl-carbonyl]-1-(pyrrolidin-1-yl-carbonyl)benzene (Compound No. 94).

Further, terephthalamide derivatives of the above formula 1 according to the present invention may form its pharmaceutically acceptable acid-addition salts with acid in accordance with some ordinary methods in the art to which the present invention pertains. For example, the acid-addition salts may include inorganic acids(e.g., hydrochloric acid, hydrobromic acid, phosphoric acid or sulfuric acid) or organic acids(e.g., formic acid, acetic acid, propionic acid, oxalic acid, citric acid, maleic acid or methanesulfonic acid).

Since terephthalamide derivatives of the above formula 1 according to the present invention has potent effects against the proliferation of HBV and HIV, it may be used as a clinically useful anti-hepatitis B agent and anti-AIDS agent.

Therefore, the present invention includes pharmaceutical compositions containing the terephthalamide derivatives of the above formula 1, and its pharmaceutically acceptable salts as active ingredients.

When pharmaceutical compositions of the present invention is intended for clinical application, it may be formulated into several dosage forms containing some exipients commonly used in pharmaceutical field; for example, oral preparations(e.g., tablets, capsules, trochel, solutions or suspensions); injectables(e.g., injectable solution or suspension, or injectable dry powder which can be immediately used by adding water for injection prior to injection); topical preparations(e.g., ointments, creams or solutions).

The vehicles used for pharmaceutical compositions of the present invention are common types available in the pharmaceutical field, which include; binders, lubricants, disintegrants, excipients, solubilizers, diluents, stabilizers, suspending agent, pigments, flavors, etc. for oral preparations; preservatives, solubilizers, stabilizers, etc. for injectable preparations; bases, diluents, lubricants preservatives, etc. for topical preparations. The pharmaceutical preparations may be administered orally or parenterally(e.g., intravenously, subcutaneously, intraperitoneally or topically). Some drugs may be formulated as an enteric coated tablet when they are unstable in gastric condition.

Further the clinical dose of terephthalamide derivatives of the above formula 1 in patients, may be appropriately determined according to therapeutic efficacy and bioavailability of active ingredients in the body, their metabolism and excretion rate, and age, sex, stage of target diseases of the patient but generally, the daily dose of adult should be given at 10~500 mg, preferably at 50~300 mg. Therefore, when pharmaceutical compositions of the present invention is prepared as an unit dosage form, the formulation of each unit should be made available so as to contain 10~500 mg of terephthalamide derivatives of the above formula 1, preferably 50~300 mg, in consideration of the above mentioned effective dose. These preparations may be administered at certain intervals of several times(preferably one to 6 times) in accordance with medical doctor or pharmacist's direction.

The present invention also includes a process of preparing terephthalamide derivatives of the present invention of the above formula 1. And the terephthalamide derivatives may be prepared by the following reaction schemes 1, 2 and 3.

The following reaction scheme 1 is a schematic diagram showing a process of preparing terephthalamide derivatives of the above formula 1 as a desired product by reacting a compound of the formula 2 and some amine compounds.

[Reaction scheme 1]

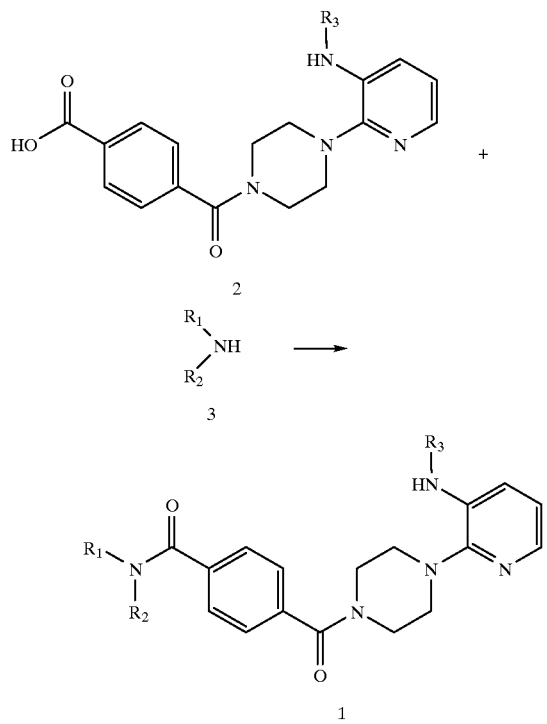

Wherein: $R_1$, $R_2$ and $R_3$ are the same as defined in the above, respectively.

According to the reaction scheme 1, terephthalic acid derivatives of the formula 2, is reacted with some acid chloride(e.g., pivaloyl chloride) to form an acid anhydride with good reactivity; then, the intermediate is further reacted with amine compounds of the formula 3, to obtain terephthalamide derivatives of the above formula 1 as a desired product. Such reaction is completed at 0~30° C. within 6 hours in the presence of the general tertiary organic bases such as triethylamine, N,N-diisopropylethylamine, N-methylmorpholine, N-methylpiperidine, 4-dimethylaminopyridine, N,N-dimethylaniline, 2,6-lutidine or pyridine. It is preferred to use a single solvent or co-solvent selected from chloroform, methylene chloride, acetonitrile, tetrahydrofuran, dioxane, dioxolane, N,N-dimethylformamide, N,N-dimethylacetamide and N-methylpyrrolidone.

Another direct process of preparing terephthalamide derivatives of the above formula 1 as a desired product via reaction between a compound of the following formula 4, a precursor of a compound of formula 2 used in the above reaction scheme 1 and some amine compounds and its preparing process is illustrated in the following reaction scheme 2. Namely, this method has an advantage of shortening one processing step of starting material.

[Reaction scheme 2]

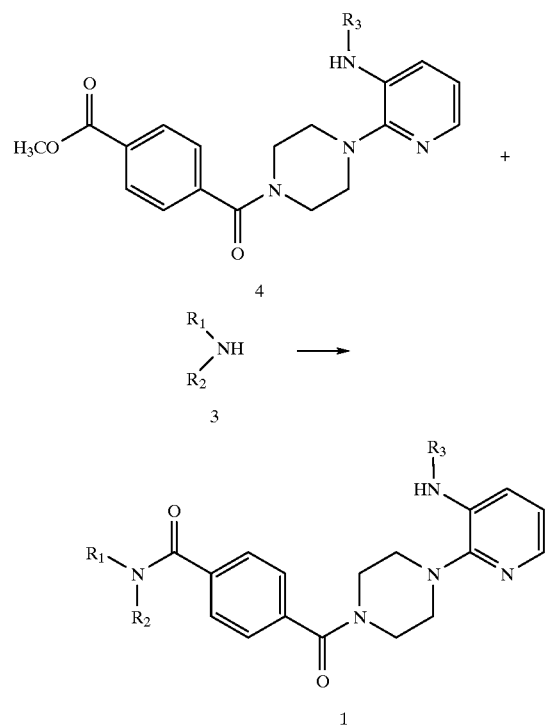

Wherein: $R_1$, $R_2$ and $R_3$ are the same as defined in the above, respectively.

According to the reaction scheme 2, the reaction is carried out under direct nucleophilic substitution between amine compounds of the formula 3 and methyl ester group of terephthalic acid ester derivatives of the formula 4. Since the reactivity of the reaction scheme 2 is relatively lower than that of the reaction scheme 1 using acid anhydride with good reactivity, more vigorous reaction conditions should be required.

The nucleophilic substitution reaction is completed at 40~90° C. within 20 hours using some alcoholic solvents (e.g., methanol, ethanol, propanol, isopropanol or butanol) or polar organic solvents(e.g., acetonitrile, N,N-dimethylformamide, N,N-dimethylacetamide or N-methylpyrrolidone).

Further, the amine compounds of the formula 3 used in the reaction scheme 1 and 2, are reagents intended for introducing the substituents $R_1$ and $R_2$ into terephthalamide derivatives of the formula 1 as a desired product. Some appropriate amine compounds, selected by required substituents, may be easily used by a person having ordinary skill in the art to which the this invention pertains.

Further, in case that $R_1$ and $R_2$ combine with nitrogen atom to form a piperazine ring, a desired product can be prepared by the following reaction scheme 3 in addition to the reaction scheme 1 and 2.

isopropanol, butanol, acetonitrile, N,N-dimethylformamide, N,N-dimethylacetamide or N-methylpyrrolidone. The reaction is quantitatively carried out at 50~110° C. within 30 hours in the presence of tertiary organic bases such as triethylamine, N-methylmorpholine, N-methylpiperidine or 2,6-lutidine.

Further, in the process of preparing compounds of the formula 1 based on the reaction scheme 1 and 2, each compound used as a starting material of the formula 2 or 4,

[Reaction scheme 3]

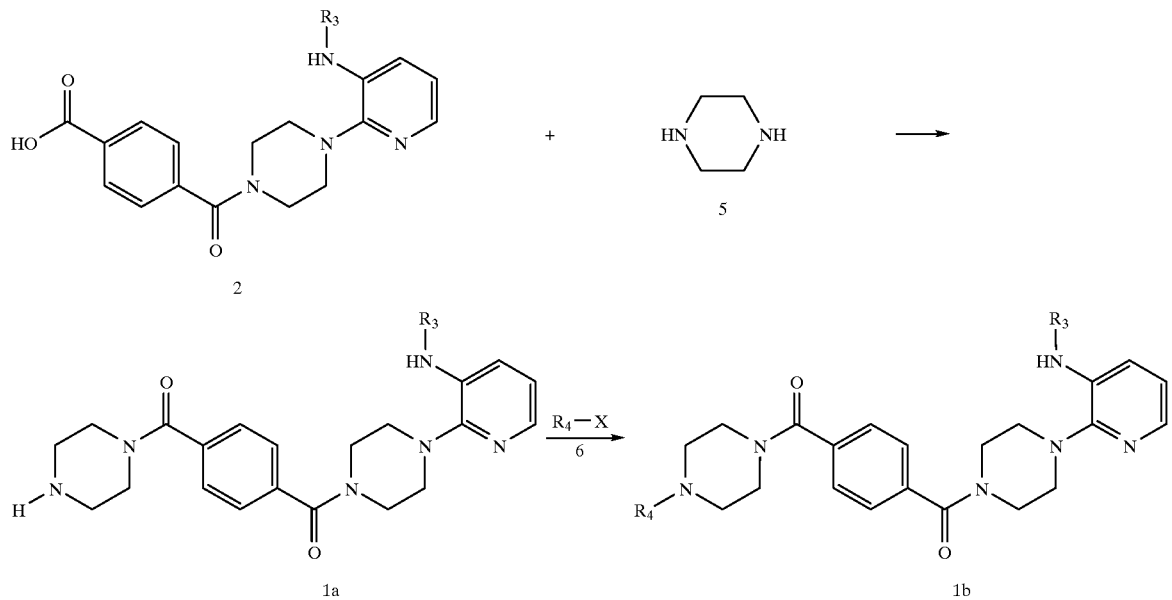

Wherein:

$R_3$ is the same as defined in the formula 1;

$R_4$ represents hydrogen atom, $C_1$~$C_5$ alkyl group, $C_3$-$C_6$ cycloalkyl group, $C_2$~$C_5$ hydroxyalkyl group, $C_2$~$C_4$ dihydroxyalkyl group, $C_3$~$C_5$ (hydroxyalkoxy)alkyl group, $C_1$~$C_3$ alkyl-substituted $C_1$~$C_4$ hydroxyalkyl group, (2R)-3-hydroxy-2-methylpropyl or (2S)-3-hydroxy-2-methylpropyl group;

X represents halogen atom.

Reaction is carried out in such a manner that terephthalic acid derivatives of the formula 2 as a starting material of the reaction scheme 1, is reacted with some acid chloride(e.g., pivaloyl chloride) to form an acid anhydride with good reactivity; then, the intermediate is further reacted with piperazine of the formula 5, to obtain terephthalamide derivatives of the above mentioned formula 1a as a desired product. Such reaction is completed at 0~30° C. within 6 hours in the presence of excess of piperazine of the formula 5, or the general tertiary organic bases such as triethylamine, pyridine, 4-dimethylaminopyridine, N,N-dimethylaniline, N-methylpiperidine, N-methylmorpholine or 2,6-lutidine. It is preferred to use the solvent selected from methylene chloride, chloroform or acetonitrile.

In addition, in case that other different substituent is intended for introduction at 4-position of the piperazine ring, the substitution reaction is carried out between terephthalamide derivatives of the formula 1a and halogen compounds of the formula 6. It is preferred to carry out the substitution reaction in polar solvents such as methanol, ethanol, respectively, can be prepared by the following reaction scheme 4 prior to use.

[Reaction scheme 4]

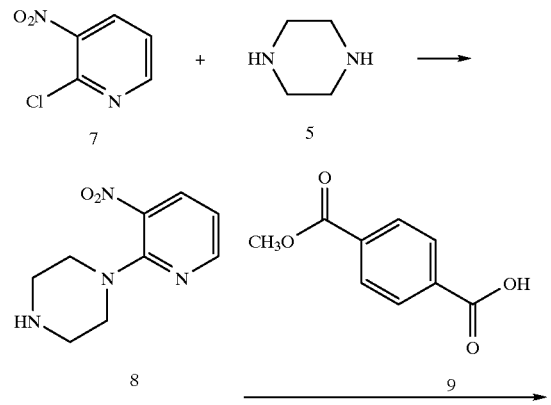

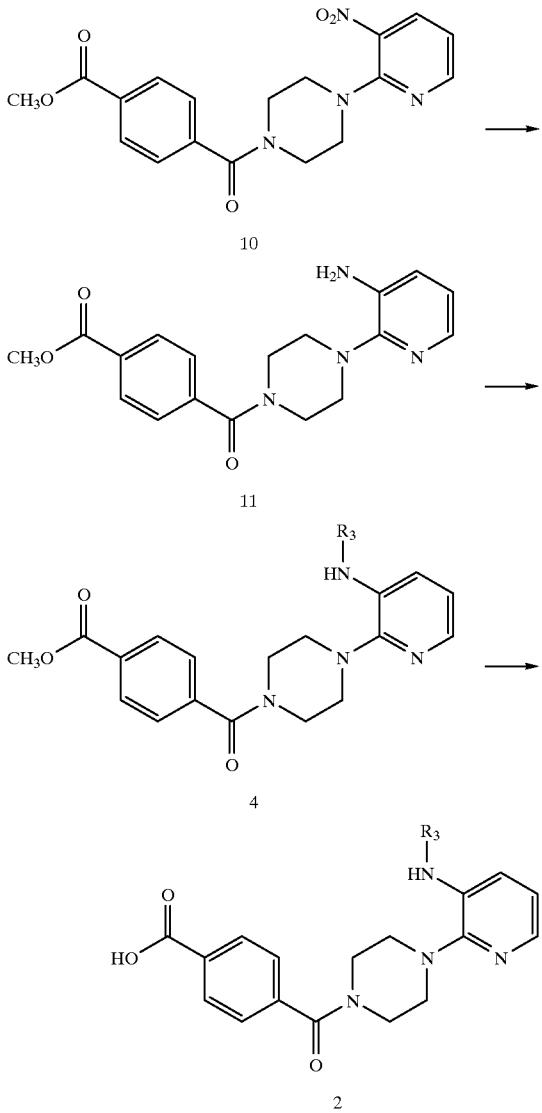

Wherein: $R_3$ is the same as defined in the formula 1.

The raw materials used for the reaction scheme 4(e.g., 2-chloro-3-nitropyridine of the formula 7, piperazine of the formula 5, and mono-methyl terephthalate of the formula 9 have been currently on the market and may be easily purchased. Further, pyridylpiperazine derivative of the formula 8 is a known compound listed in literatures and may be easily prepared by the known process [*J. Med. Chem.*, 1994, Vol. 37, 999~1014] prior to use.

First, mono-methyl terephthalate of the formula 9 is reacted with some acid chloride(e.g., pivaloyl chloride) to form an acid anhydride with good reactivity; then, the intermediate is further reacted with pyridylpiperazine derivative of the formula 8, to obtain terephthalic acid ester derivative including nitropyridyl group of the above mentioned formula 10. Such reaction is completed at 0~30° C. within 5 hours in the presence of tertiary organic bases. The main solvents used for this reaction include some non-polar solvents such as methylene chloride, chloroform, etc.

The compound of the formula 10 is reduced by catalytic hydrogenation to give the compound including aminopyridyl group of the formula 11. Such reduction may be well carried out under high-pressure condition using hydrogen gas in the presence of small amounts of activated metal catalysts such as Raney-nickel or palladium on activated carbon, being widely used in the reductive reaction. Various solvents such as methanol, ethanol, methylene chloride, chloroform or ethyl acetate may be used for this reaction.

Further, the compound including aminopyridyl group of the formula 11 are under reductive alkylation with acetone or acetaldehyde in the presence of a selective reducing agent such as sodium cyanoborohydride under acidic conditions to form terephthalic acid ester derivatives including isopropylamino or ethylamino group, expressed by the formula 4.

Such reaction may be well carried out in the presence of some organic acids such as acetic acid and in general, alcoholic solvents such as methanol or ethanol are used.

When terephthalic acid ester derivatives, so formed and expressed by the formula 4 are hydrolyzed, terephthalic acid derivatives of the formula 2 is obtained and the solvents used for this reaction include a co-solvent where water is added to lower alcohols such as methanol, ethanol or isopropanol. The hydrolysis is completed at below 40° C. within 3 hours.

The present invention is explained in more detail by the following preparations examples and examples but is not limited by these examples.

PREPARATION EXAMPLE 1

Preparation of 1-(3-nitro-2-pyridyl)piperazine

Anhydrous piperazine (60 g) was dissolved in methylene chloride (400 ml) and then, 2-chloro-3-nitropyridine (40 g) was added slowly at 10~20° C. and the mixture was stirred at 20° C. for 2 hours. After completion of the reaction, the reaction mixture was washed with water (300 ml) three times and the separated organic layers were concentrated under reduced pressure. The precipitate was washed with water and small amount of ethanol and dried in vacuo to give 46 g (yield: 87.5%) of the desired compound.

m.p.: 79~82° C.; $^1$H-NMR(CDCl$_3$), ppm: δ 1.93(s, 1H), 2.95(m, 4H), 3.41(m, 4H), 6.71(m, 1H), 8.10(m, 1H), 8.30 (m, 1H)

PREPARATION EXAMPLE 2

Preparation of 4-[1-(3-nitro-2-pyridyl)piperazin-4-yl-carbonyl]benzoic acid methyl ester To the solution of mono-methyl terephthalate (20 g) in methylene chloride (380 ml), triethylamine (18.2 ml) was added and cooled. Then, pivaloyl chloride (15 ml) was added to the solution at 0~5° C. and stirred at 5° C. for 2 hours. 1-(3-Nitro-2-pyridyl)piperazine (21.3 g) and triethylamine (18.6 ml) were added to the reaction mixture in order and the mixture was stirred at 5~10° C. for 2 hours. The reaction mixture was washed with aqueous sodium bicarbonate and water twice and the separated organic layers were concentrated under reduced pressure. The precipitated yellow solid was treated with ether (250 ml) for 1 hour, filtered and dried to give 17.2 g (yield:

91%) of the desired compound as bright yellow crystal.

m.p.: 149~152° C.; $^1$H-NMR(CDCl$_3$), ppm: δ 3.38(m, 2H), 3.53(m, 4H), 3.92(m, 5H), 6.81(m, 1H), 7.48(m, 2H), 8.08(m, 2H), 8.17(m, 1H), 8.35(m, 1H)

PREPARATION EXAMPLE 3

Preparation of 4-[1-(3-amino-2-pyridyl)piperazin-4-yl-carbonyl]benzoic acid methyl ester 4-[1-(3-Nitro-2-pyridyl)piperazin-4-yl-carbonyl]benzoic acid methyl ester (5 g) was dissolved in a co-solvent of methanol (80 ml) and methylene chloride (60 ml) in a pressurized reactor. With the addition of about 1 g of Raney-nickel (50% slurry in water), the reaction mixture was filled with hydrogen gas and stirred at 50~60 psi for 4 hours. After completion of the reaction, reaction mixture was filtered through celite and filtrate was concentrated under reduced pressure. The concentrated residue was treated with hexane and ether for crystallization, filtered, washed and dried to give 4.05 g (yield: 88%) of the desired compound.

m.p.: 144° C.; $^1$H-NMR(CDCl$_3$), ppm: δ 3.15(m, 4H), 3.47(m, 2H), 3.82~3.91(m, 7H), 6.87(m, 1H), 6.97(m, 1H), 7.48(m, 2H), 7.78(m, 1H), 8.07(m, 2H)

PREPARATION EXAMPLE 4

Preparation of 4-[1-[3-(isopropylamino)-2-pyridyl]piperazin-4-yl-carbonyl]benzoic acid methyl ester 4-[1-(3-Amino-2-pyridyl)piperazin4-yl-carbonyl]benzoic acid methyl ester (4 g) was dissolved in methanol (90 ml) and then, acetone (2 ml), acetic acid (5 ml) and sodium cyanoborohydride (2.4 g) were added at 10° C. in order. The reaction mixture was stirred at 10° C. for 4 hours and heated to 20~25° C. and stirred for 1 hour. The solution was neutralized (pH=~8) by addition of aqueous 3N-sodium hydroxide, and excess of water was added gradually for precipitation. The mixture was stirred for 1 hour, filtered, washed with water, methanol and ether in order and dried to give 3.5 g (yield: 78%) of the desired compound as white crystal.

m.p.: 116~118° C.; $^1$H-NMR(CDCl$_3$), ppm: δ 1.24(d, 6H), 3.12(m, 4H), 3.53(m, 3H), 3.91(m, 5H), 4.14(m, 1H), 7.02(m, 1H), 7.08(m, 1H), 7.49(m, 1H), 5 7.76(m, 1H), 8.08(m, 2H)

PREPARATION EXAMPLE 5

Preparation of 4-[1-[3-(isopropylamino)-2-pyridyl]piperazin-4-yl-carbonyl]benzoic acid 4-[1-[3-(Isopropylamino)-2-pyridyl]piperazin-4-yl-carbonyl] benzoic acid methyl ester (3 g) was dissolved in methanol (47 ml) and then, aqueous 1N-sodium hydroxide (16 ml) was added slowly. The solution was stirred at 20~25° C. for 3 hours. 2N-HCl was added slowly to the mixture for neutralization (pH=~5) and then, the crystalline powder was precipitated. The crystalline powder was filtered, washed with water and methanol and dried to give 2.7 g (yield: 93%) of the desired compound.

m.p.: 215~217° C.; $^1$H-NMR(CDCl$_3$), ppm: δ 1.24(d, 6H), 3.17(m, 4H), 3.56(m, 3H), 3.93(m, 2H), 6.91(m, 1H), 7.03(m, 1H), 7.56(m, 2H), 7.87(m, 1H), 8.16(m, 2H)

PREPARATION EXAMPLE 6

Preparation of 4-[1-[3-(ethylamino)-2-pyridyl]piperazin-4-yl-carbonyl]benzoic acid methyl ester 4-[1-(3-Amino-2-pyridyl)piperazin-4-yl-carbonyl]benzoic acid methyl ester (4 g) was dissolved in methanol (80 ml) and then, acetaldehyde (1.7 ml) and acetic acid (4 ml) were added at 0° C. The solution was stirred at 0° C. for 30 minutes. Then, with the addition of sodium cyanoborohydride (2.2 g), the solution was stirred at 0~5° C. for 2 hours. Excess of water was added gradually, and the solution was neutralized (pH=~8) by addition of aqueous 3N-sodium hydroxide. The mixture was stirred for 1 hour and filtered, and the crude solid was recrystallized using methanol and ether to give 3.51 g (yield: 81%) of the desired compound.

m.p.: 96~97° C.; $^1$H-NMR(CDCl$_3$), ppm: δ 1.28(t, 3H), 3.12(m, 1H), 3.52(m, 2H), 3.92(m, 5H), 4.18(m, 1H), 6.85 (m, 1H), 6.96(m, 1H), 7.48(m, 2H), 7.70(m, 1H), 8.06(m, 2H)

PREPARATION EXAMPLE 7

Preparation of 4-[1-[3-(ethylamino)-2-pyridyl]piperazin-4-yl-carbonyl]benzoic acid By the same procedure as described in the preparation example 5, 4-[1-[3-(ethylamino)-2-pyridyl]piperazin-4-yl-carbonyl]benzoic acid methyl ester was hydrolyzed to give a desired product.

Yield: 91%; m.p.: 208~209° C.; $^1$H-NMR(CDCl$_3$), ppm: δ 1.30(t, 3H), 3.16(m, 6H), 3.48(m, 2H), 3.94(m, 2H), 6.95(m, 1H), 7.05(m, 1H), 7.56(m, 2H), 7.91(m, 1H), 8.15 (m, 2H)

EXAMPLE 1

1-[N-(2-Hydroxyethyl)carbamoyl]-4-[1-[3-(isopropylamino)-2-pyridyl]piperazin-4-yl-carbonyl]benzene 4-[1-[3-(Isopropylamino)-2-pyridyl]piperazin-4-yl-carbonyl]benzoic acid (1.5 g) was dissolved in methylene chloride (50 ml) and then, triethylamine (0.7 ml) was added and cooled. Pivaloyl chloride(0.58 ml) was added slowly to the solution at 0~5° C. and the mixture was stirred at 5° C. for 2 hours. And then, triethylamine (0.7 ml) and 2-aminoethanol(1.27 g) were added in order, the solution was stirred at 0~5° C. for 2 hours and heated slowly to 20~25° C. and stirred for 30 minutes. The reaction mixture was washed with water twice and the solvent was concentrated under reduced pressure. The concentrated residue was crystallized by treatment with ether and further recrystallized using isopropanol and ether. The recrystallized product was filtered and dried to give 1.34 g (yield: 80%) of the desired compound as a white powder.

m.p.: 182~184° C.; $^1$H-NMR(CDCl$_3$), ppm: δ 1.20(d, 6H), 3.07(m, 4H), 3.51(m, 3H), 3.58(m, 2H), 3.76(m, 2H), 3.85(m, 2H), 6.83(m, 1H), 6.94(m, 1H), 7.07(m, 1H), 7.36 (m, 2H), 7.63(m, 1H), 7.77(m, 2H)

EXAMPLE 2

1-[N-(3-Hydroxypropyl)carbamoyl]-4-[1-[3-(isopropylamino)-2-pyridyl]piperazin-4-yl-carbonyl]benzene By the same procedure as described in the example 1, synthesis was carried out starting with 4-[1-[3-(isopropylamino)-2-pyridyl]piperazin-4-yl-carbonyl]benzoic acid and using 3-amino-1-propanol. Then, the product was recrystallized using ethyl acetate and ether to give the desired compound.

Yield: 76%; m.p.: 110~111° C.; $^1$H-NMR(CDCl$_3$), ppm: δ 1.23(d, 6H), 1.80(m, 2H), 3.11(m, 4H), 3.50(m, 3H), 3.59(m, 2H), 3.72(m, 2H), 3.90(m, 2H), 4.15(m, 1H), 6.86 (m, 1H), 6.97(m, 1H), 7.12(m, 1H), 7.44(m, 2H), 7.67(m, 1H), 7.78(m, 2H)

EXAMPLE 3

1-[N-(4-Hydroxybutyl)carbamoyl]-4-[1-[3-(isopropylamino)-2-pyridyl]piperazin-4-yl-carbonyl]benzene By the same procedure as described in the example 1, synthesis was carried out starting with 4-[1-[3-

(isopropylamino)-2-pyridyl]piperazin-4-yl-carbonyl] benzoic acid and using 4-amino-1-butanol. Then, the product was recrystallized using ethyl acetate and isopropyl ether to give the desired compound.

Yield: 84%; $^1$H-NMR(CDCl$_3$), ppm: δ 1.22(d, 6H), 1.51 (m, 2H), 1.62(m, 2H), 3.10(m, 4H), 3.51(m, 5H), 3.73(m, 2H), 3.92(m, 2H), 4.13(m, 1H), 6.84(m, 1H), 6.95(m, 1H), 7.11(m, 1H), 7.45(m, 2H), 7.64(m, 1H), 7.79(m, 2H)

EXAMPLE 4

1-[N-(5-Hydroxypentyl)carbamoyl]-4-[1-[3-(isopropylamino)-2-pyridyl]piperazin-4-yl-carbonyl] benzene The desired compound was obtained by the same synthetic method as described in the Example 1.

Yield: 74%; $^1$H-NMR(CDCl$_3$), ppm: δ 1.22(d, 6H), 1.42~1.51(m, 6H), 3.10(m, 4H), 3.50(m, 5H), 3.71(m, 2H), 3.91(m, 2H), 4.13(m, 1H), 6.82(m, 1H), 6.94(m, 1H), 7.10 (m, 1H), 7.44(m, 2H), 7.64(m, 1H), 7.77(m, 2H)

EXAMPLE 5

1-[N-(2-Hydroxyethyl)-N-methylcarbamoyl]-4-[1-[3-(isopropylamino)-2-pyridyl]piperazin-4-yl-carbonyl]benzene The desired compound was obtained by the same synthetic method as described in the Example 1.

Yield: 77%; m.p.: 131~132° C.; $^1$H-NMR(CDCl$_3$), ppm: δ 1.21(d, 6H), 3.02(s, 3H), 3.11(m, 4H), 3.53(m, 3H), 3.72(m, 2H), 3.89(m, 3H), 4.15(m, 1H), 6.84(m, 1H), 6.95 (m, 1H), 7.48(m, 4H), 7.68(m, 1H)

EXAMPLE 6

1-[N-Ethyl-N-(2-hydroxyethyl)carbamoyl]-4-[1-[3-(isopropylamino)-2-pyridyl]piperazin-4-yl-carbonyl] benzene By the same procedure as described in the example 1, synthesis was carried out starting with 4-[1-[3-(isopropylamino)-2-pyridyl]piperazin-4-yl-carbonyl] benzoic acid and using 2-(ethylamino)ethanol. Then, the product was recrystallized using ethyl acetate and petroleum ether, filtered and dried to give the desired compound as white crystal.

Yield: 86%; m.p.: 115° C.; $^1$H-NMR(CDCl$_3$), ppm: δ 1.11(t, 3H), 1.20(d, 6H), 3.06(m, 4H), 3.31(m, 2H), 3.52(m, 4H), 3.68(m, 2H), 3.87(m, 3H), 4.14(m, 1H), 6.83(m, 1H), 6.93(m, 1H), 7.45(m, 4H), 7.66(m, 1H)

EXAMPLE 7

1-[N-(2-Hydroxyethyl)-N-propylcarbamoyl]-4-[1-[3-(isopropylamino)-2-pyridyl]piperazin-4-yl-carbonyl] benzene The desired compound was obtained by the same synthetic method as described in the Example 6.

Yield: 82%; m.p.: 79~82° C.; $^1$H-NMR(CDCl$_3$), ppm: δ 0.77(t, 3H), 1.23(d, 6H), 1.56(m, 2H), 3.14~3.24(m, 6H), 3.53(m, 4H), 3.70(m, 2H), 3.89(m, 3H), 4.15(m, 1H), 6.91 (m, 1H), 6.98(m, 1H), 7.46(m, 4H), 7.70(m, 1H)

EXAMPLE 8

1-[N-(2-Hydroxyethyl)-N-(1-methylethyl) carbamoyl]-4-[1-[3-(isopropylamino)-2-pyridyl] piperazin-4-yl-carbonyl]benzene The desired compound was obtained by the same synthetic method as described in the Example 6.

Yield: 85%; $^1$H-NMR(CDCl$_3$), ppm: δ 1.21(m, 12H), 3.06(m, 4H), 3.51(m, 6H), 3.80(m, 2H), 3.91(m, 2H), 4.13 (m, 1H), 6.90(m, 1H), 6.97(m, 1H), 7.47(m, 4H), 7.70(m, 1H)

EXAMPLE 9

1-[N-Butyl-N-(2-hydroxyethyl)carbamoyl]-4-[1-[3-(isopropylamino)-2-pyridyl]piperazin-4-yl-carbonyl] benzene The desired compound was obtained by the same synthetic method as described in the Example 6.

Yield: 75%; $^1$H-NMR(CDCl$_3$), ppm: δ 0.79(t, 3H), 1.21 (d, 6H), 1.48(m, 4H), 3.20(m, 6H), 3.52(m, 4H), 3.70(m, 2H), 3.88(m, 3H), 4.13(m, 1H), 6.90(m, 1H), 6.97(m, 1H), 7.45(m, 4H), 7.70(m, 1H)

EXAMPLE 10

1-[N-Benzyl-N-(2-hydroxyethyl)carbamoyl]-4-[1-[3-(isopropylamino)-2-pyridyl]piperazin-4-yl-carbonyl] benzene By the same procedure as described in the example 1, synthesis was carried out starting with 4-[1-[3-(isopropylamino)-2-pyridyl]piperazin-4-yl-carbonyl] benzoic acid and using 2-(benzylamino)ethanol. Then, the product was recrystallized using isopropanol and isopropyl ether, filtered and dried to give the desired compound.

Yield: 81%; m.p.: 99~101° C.; $^1$H-NMR(CDCl$_3$), ppm: δ 1.22(d, 6H), 3.11(m, 4H), 3.53(m, 3H), 3.69(m, 2H), 3.81 (m, 2H), 3.89(m, 2H, 4.58(s, 2H), 6.87(m, 1H), 6.96(m, 1H), 7.16(m, 2H), 7.28(m, 1H), 7.35(m, 2H), 7.44~7.52(m, 4H), 7.68(m, 1H)

EXAMPLE 11

1-[N-(2-Hydroxyethyl)-N-phenylcarbamoyl]-4-[1-[3-(isopropylamino)-2-pyridyl]piperazin-4-yl-carbonyl]benzene The desired compound was obtained by the same synthetic method as described in the Example 10.

Yield: 76%; m.p.: 71~72° C.; $^1$H-NMR(CDCl$_3$), ppm: δ 1.21(d, 6H), 3.08(m, 4H), 3.42(m, 2H), 3.53(m, 1H), 3.84 (m, 2H), 4.21(m, 2H), 6.88(m, 1H), 6.96(m, 1H), 7.07(m, 2H), 7.16(m, 1H), 7.25(m, 4H), 7.36(m, 2H), 7.68(m, 1H)

EXAMPLE 12

1-[N,N-Bis(2-hydroxyethyl)carbamoyl]-4-[1-[3-(isopropylamino)-2-pyridyl]piperazin-4-yl-carbonyl] benzene The desired compound was obtained by the same synthetic method as described in the Example 10.

Yield: 83%; m.p.: 161~162° C.; $^1$H-NMR(CDCl$_3$), ppm: δ 1.22(d, 6H), 3.13(m, 4H), 3.41(m, 2H), 3.56(m, 3H), 3.70(m, 5H), 3.96(m, 3H), 6.89(m, 1H), 6.97(m, 1H), 7.49 (m, 2H), 7.55(m, 2H), 7.68(m, 1H)

EXAMPLE 13

1-[N,N-Diethylcarbamoyl]-4-[1-[3-(isopropylamino)-2-pyridyl]piperazin-4-yl-carbonyl] benzene The desired compound was obtained by the same synthetic method as described in the Example 1.

Yield: 80%; m.p.: 78~80° C.; ¹H-NMR(CDCl₃), ppm: δ 1.08(t, 3H), 1.22(m, 9H), 3.11(m, 4H), 3.21(m, 2H), 3.53(m, 5H), 3.91(m, 2H), 4.15(m, 1H), 6.84(m, 1H), 6.95(m, 1H), 7.39(m, 2H), 7.44(m, 2H), 7.68(m, 1H)

EXAMPLE 14

1-[N,N-Bis(1-methylethyl)carbamoyl]-4-[1-[3-(isopropylamino)-2-pyridyl]piperazin-4-yl-carbonyl]benzene The desired compound was obtained by the same synthetic method as described in the Example 1.

Yield: 72%; m.p.: 152~153° C.; ¹H-NMR(CDCl₃), ppm: δ 1.16(m, 6H), 1.24(d, 6H), 1.50(m, 6H), 3.14(m, 4H), 3.53(m, 3H), 3.87(m, 4H), 6.90(m, 1H), 6.97(m, 1H), 7.36 (m, 2H), 7.48(m, 2H), 7.69(m, 1H)

EXAMPLE 15

1-[N,N-Bis(2-hydroxypropyl)carbamoyl]-4-[1-[3-(isopropylamino)-2-pyridyl]piperazin-4-yl-carbonyl]benzene The desired compound was obtained by the same synthetic method as described in the Example 10.

Yield: 77%; m.p.: 73~75° C.; ¹H-NMR(CDCl₃), ppm: δ 1.11(d, 3H), 1.21(d, 9H), 3.05(m, 4H), 3.51(m, 5H), 3.80(m, 4H), 4.10(m, 2H), 6.82(m, 1H), 6.93(m, 1H), 7.46(m, 4H), 7.66(m, 1H)

EXAMPLE 16

1-[N-[2-(2-Hydroxyethoxy)ethyl]carbamoyl]-4-[1-[3-(isopropylamino)-2-pyridyl]piperazin-4-yl-carbonyl]benzene The desired compound was obtained by the same synthetic method as described in the Example 1.

Yield: 82%; m.p.: 116° C.; ¹H-NMR(CDCl₃), ppm: δ 1.21(d, 6H), 3.10(m, 4H), 3.51(m, 3H), 3.60(m, 2H), 3.68 (m, 4H), 3.76(m, 2H), 3.90(m, 2H), 4.16(m, 1H), 6.84(m, 1H), 6.95(m, 2H), 7.44(m, 2H), 7.67(m, 1H), 7.80(m, 2H)

EXAMPLE 17

1-[N-Ethyl-N-(2-hydroxyethyl)carbamoyl]-4-[1-[3-(ethylamino)-2-pyridyl]piperazin-4-yl-carbonyl]benzene By the same procedure as described in the example 1, synthesis was carried out starting with 4-[1-[3-(ethylamino)-2-pyridyl]piperazin-4-yl-carbonyl]benzoic acid and using 2-(ethylamino)ethanol. Then, the product was recrystallized using ethyl acetate and hexane to give the desired compound.

Yield: 72%; m.p.: 106~108° C.; ¹H-NMR(CDCl₃), ppm: δ 1.12(t, 3H), 1.26(t, 3H), 3.12(m, 6H), 3.30(m, 2H), 3.53 (m, 3H), 3.69(m, 2H), 3.89(m, 3H), 4.19(m, 1H), 6.84(m, 1H), 6.95(m, 1H), 7.48(m, 4H), 7.70(m, 1H)

EXAMPLE 18

1-[4-[1-[3-(Isopropylamino)-2-pyridyl]piperazin-4-yl-carbonyl]benzoyl]piperazine 4-[1-[3-(Isopropylamino)-2-pyridyl]piperazin-4-yl-carbonyl]benzoic acid (1.5 g) was dissolved in methylene chloride (50 ml) and then, triethylamine (0.7 ml) was added and cooled. Pivaloyl chloride (0.58 ml) was added slowly to the solution at 0~5° C. and the mixture was stirred at 5° C. for 2 hours. With the addition of piperazine (0.9 g), the solution was stirred at 5~10° C. for 3 hours. The reaction mixture was washed with water and aqueous sodium bicarbonate and the solvent was concentrated under reduced pressure. The concentrated residue was crystallized by treatment with ether and further recrystallized using isopropanol and ether. The recrystallized product was filtered and dried to give 1.48 g (yield: 83%) of the desired compound as white crystal.

m.p.: 175~176° C.; ¹H-NMR(CDCl₃), ppm: δ 1.21(d, 6H), 2.51(m, 1H), 2.84(m, 2H), 3.03(m, 6H), 3.52(m, 5H), 3.80(m, 2H), 3.90(m, 2H), 4.13(m, 1H), 6.80(m, 1H), 6.93 (m, 1H), 7.47(m, 4H), 7.66(m, 1H)

EXAMPLE 19

1-[4-[1-[3-(Isopropylamino)-2-pyridyl]piperazin-4-yl-carbonyl]benzoyl]-4-methylpiperazine 4-[1-[3-(Isopropylamino)-2-pyridyl]piperazin-4-yl-carbonyl]benzoic acid (1.2 g) was dissolved in methylene chloride (40 ml) and then, triethylamine (0.6 ml) was added and cooled. Pivaloyl chloride (0.46 ml) was added slowly to the solution at 0~5° C. and the mixture was stirred at 5° C. for 2 hours. With the addition of triethylamine (0.6 ml) and 1-methylpiperazine (0.38 g), the reaction mixture was stirred at 5° C. for 2 hours and heated slowly to 20° C. and stirred for 30 minutes. The reaction mixture was washed with water and aqueous sodium bicarbonate and the solvent was concentrated under reduced pressure. The concentrated residue was crystallized by treatment with hexane and ether, and further recrystallized using ethyl acetate and isopropyl ether. The recrystallized product was filtered and dried to give 1.15 g (yield: 78%) of the desired compound as white powder.

m.p.: 158~160° C.; ¹H-NMR(CDCl₃), ppm: δ 1.20(d, 6H), 2.33(m, 5H), 2.54(m, 2H), 3.05(m, 4H), 3.47(m, 5H), 3.85(m, 4H), 4.12(m, 1H), 6.82(m, 1H), 6.90(m, 1H), 7.45 (m, 4H), 7.65(m, 1H)

EXAMPLE 20

4-Ethyl-1-[4-[1-[3-(isopropylamino)-2-pyridyl]piperazin-4-yl-carbonyl]benzoyl]piperazine The desired compound was obtained by the same synthetic method as described in the Example 19.

Yield: 85%; m.p.: 130~131° C.; ¹H-NMR(CDCl₃), ppm: δ 1.07(t, 3H), 1.20(d, 6H), 2.51(m, 6H), 3.05(m, 4H), 3.51(m, 5H), 3.89(m, 4H), 4.13(m, 1H), 6.81(m, 1H), 6.93 (m, 1H), 7.46(m, 4H), 7.66(m, 1H)

EXAMPLE 21

4-Cyclopentyl-1-[4-[1-[3-(isopropylamino)-2-pyridyl]piperazin-4-yl-carbonyl]benzoyl]piperazine 1-[4-[1-[3-(Isopropylamino)-2-pyridyl]piperazin-4-yl-carbonyl]benzoyl]piperazine (0.5 g) was dissolved in acetonitrile (25 ml) and then, N-methylmorpholine (0.17 ml) and cyclopentyl bromide (0.3 ml) were added. The solution was heated to 65~75° C. and stirred for 20 hours. The solvent was concentrated under reduced pressure and then, the residue was dissolved in chloroform (40 ml). The solution was washed with water twice and the solvent was concentrated under reduced pressure. The concentrated residue was crystallized by treatment with ether and hexane, and further recrystallized using ethanol and isopropyl ether. The recrystallized product was filtered and dried to give 0.41 g (yield: 71%) of the desired compound.

m.p.: 181~182° C.; ¹H-NMR(CDCl₃), ppm: δ 1.22(d, 6H), 1.41(m, 2H), 1.53(m, 2H), 1.69(m, 1H), 1.85(m, 2H), 2.42(m, 2H), 2.57(m, 2H), 3.04(m, 4H), 3.43(m, 2H), 3.51(m, 3H), 3.81(m, 4H), 4.14(m, 1H), 6.81(m, 1H), 6.91(m, 1H), 7.45(m, 4H), 7.66(m, 1H)

EXAMPLE 22

4-(2-Hydroxyethyl)-1-[4-[1-[3-(isopropylamino)-2-pyridyl]piperazin-4-yl-carbonyl]benzoyl]piperazine By the same procedure as described in the example 19, synthesis was carried out starting with 4-[1-[3-(isopropylamino)-2-pyridyl]piperazin-4-yl-carbonyl]benzoic acid and using 1-(2-hydroxyethyl)piperazine. Then, the product was recrystallized using isopropanol and ether to give the desired compound.

Yield: 82%; m.p.: 148~149° C.; ¹H-NMR(CDCl₃), ppm: δ 1.23(d, 6H), 2.49(m, 2H), 2.62(m, 4H), 3.05(m, 4H), 3.52(m, 5H), 3.65(m, 2H), 3.84(m, 4H), 4.11(m, 1H), 6.80(m, 1H), 6.91(m, 1H), 7.45(m, 4H), 7.66(m, 1H)

EXAMPLE 23

4-(3-Hydroxypropyl)-1-[4-[1-[3-(isopropylamino)-2-pyridyl]piperazin-4-yl-carbonyl]benzoyl]piperazine 1-[4-[1-[3-(Isopropylamino)-2-pyridyl]piperazin-4-yl-carbonyl]benzoyl]piperazine (0.5 g) was dissolved in anhydrous ethanol (25 ml) and then, triethylamine (0.3 ml) and 3-bromo-1-propanol (0.5 g) were added. The solution was heated to reflux for 12 hours. The solvent was concentrated under reduced pressure and then, the residue was dissolved in chloroform (50 ml), and the solution was washed with water twice. Water (40 ml), methanol (5 ml) and aqueous 10% sodium hydroxide (10 ml) were added to chloroform solution and the mixture was stirred for 1 hour. The separated organic layers were washed with water and the solvent was concentrated under reduced pressure. The concentrated residue was crystallized by treatment with ether, and further recrystallized using ethyl acetate and ether, filtered and dried to give 0.44 g (yield: 78%) of the desired compound as white crystal.

m.p.: 129° C.; ¹H-NMR(CDCl₃), ppm: δ 1.22(d, 6H), 1.76(m, 2H), 2.50(m, 2H), 2.68(m, 4H), 3.04(m, 4H), 3.51(m, 5H), 3.80(m, 6H), 4.12(m, 1H), 6.80(m, 1H), 6.91(m, 1H), 7.47(m, 4H), 7.65(m, 1H)

EXAMPLE 24

4-[(2R)-3-Hydroxy-2-methylpropyl]-1-[4-[1-[3-(isopropylamino)-2pyridyl]piperazin-4-yl-carbonyl]benzoyl]piperazine The desired compound was obtained by the same synthetic method as described in the Example 23.

Yield: 75%; ¹H-NMR(CDCl₃), ppm: δ 1.01(d, 3H), 1.20(d, 6H), 2.00(m, 1H), 2.50(m, 2H) 2.67(m, 4H), 3.05(m, 4H), 3.51(m, 5H), 3.79(m, 6H), 4.11(m, 1H), 6.81(m, 1H), 6.91(m, 1H), 7.45(m, 4H), 7.66(m, 1H)

EXAMPLE 25

4-[(2S)-3-Hydroxy-2-methylpropyl]-1-1-[4-[1-[3-(isopropylamino)-2-pyridyl]piperazin4-yl-carbonyl]benzoyl]piperazine The desired compound was obtained by the same synthetic method as described in the Example 23.

Yield: 72%; ¹H-NMR(CDCl₃), ppm: δ 1.02(d, 3H), 1.21(d, 6H), 2.01(m, 1H), 2.50(m, 2H), 2.67(m, 4H), 3.06(m, 4H), 3.50(m, 5H), 3.79(m, 6H), 4.10(m, 1H), 6.80(m, 1H), 6.90(m, 1H), 7.47(m, 4H), 7.66(m, 1H)

EXAMPLE 26

4-(2,2-Dimethyl-3-hydroxypropyl)-1-[4-[1-[3-(isopropylamino)-2-pyridyl]piperazin-4-yl-carbonyl]benzoyl]piperazine The desired compound was obtained by the same synthetic method as described in the Example 23.

Yield: 80%; ¹H-NMR(CDCl₃), ppm: δ 1.04(s, 6H), 1.20(d, 6H), 2.51(m, 2H), 2.68(m, 4H), 3.06(m, 4H), 3.50(m, 5H), 3.79(m, 6H), 4.10(m, 1H), 6.80(m, 1H), 6.90(m, 1H), 7.47(m, 4H), 7.66(m, 1H)

EXAMPLE 27

4-(2,3-Dihydroxypropyl)-1-[4-[1-[3-(isopropylamino)-2-pyridyl]piperazin-4-yl-carbonyl]benzoyl]piperazine By the same procedure as described in the example 23, synthesis was carried out starting with 1-[4-[1-[3-(isopropylamino)-2-pyridyl]piperazin-4-yl-carbonyl]benzoyl]piperazine and using 3-bromo-1,2-propanediol. Then, the product was recrystallized using isopropanol and isopropyl ether to give the desired compound.

Yield: 71%; m.p.: 158° C.; ¹H-NMR(CDCl₃), ppm: δ 1.22(d, 6H), 2.47(m, 2H), 2.70(m, 6H), 3.09(m, 4H), 3.51(m, 5H), 3.75(m, 1H), 3.88(m, 6H), 4.13(m, 1H), 6.81(m, 1H), 6.91(m, 1H), 7.48(m, 4H), 7.66(m, 1H)

EXAMPLE 28

4-[2-(2-Hydroxyethoxy)ethyl]-1-[4-[1-[3-(isopropylamino)-2-pyridyl]piperazin-4-yl-carbonyl]benzoyl]piperazine The desired compound was obtained by the same synthetic method as described in the Example 19.

Yield: 80%; m.p.: 92~93° C.; ¹H-NMR(CDCl₃), ppm: δ 1.21(d, 6H), 2.55(m, 4H), 3.09(m, 4H), 3.52(m, 5H), 3.59(m, 4H), 3.69(m, 4H), 3.89(m, 4H), 4.12(m, 1H), 6.80(m, 1H), 6.91(m, 1H), 7.43(m, 4H), 7.66(m, 1H)

EXAMPLE 29

1-[4-[1-[3-(Ethylamino)-2-pyridyl]piperazin-4-yl-carbonyl]benzoyl]-4-(2-hydroxyethyl)piperazine By the same procedure as described in the example 19, synthesis was carried out starting with 4-[1-[3-(ethylamino)-2-pyridyl]piperazin-4-yl-carbonyl]benzoic acid and using 1-(2-hydroxyethyl)piperazine. Then, the product was recrystallized using ethyl acetate and hexane to give the desired compound.

Yield: 76%; m.p.: 152~153° C.; ¹H-NMR(CDCl₃), ppm: δ 1.29(t, 3H), 2.51(m, 2H), 2.63(m, 4H), 3.12(m, 6H), 3.45(m, 4H), 3.70(m, 2H), 3.87(m, 4H), 4.18(m, 1H), 6.92(m, 1H), 6.97(m, 1H), 7.46(m, 4H), 7.68(m, 1H)

EXAMPLE 30

1-[N-(1,1-Dimethyl-2-hydroxyethyl)carbamoyl]-4-[1-[3-(isopropylamino)-2-pyridyl]piperazin-4-yl-carbonyl]benzene 4-[1-[3-(Isopropylamino)-2-pyridyl]piperazin-4-yl-carbonyl]benzoic acid (1.5 g) was dissolved in methylene chloride (45 ml), and then triethylamine (0.73 ml) was added and cooled. Pivaloyl chloride (0.58 ml) was added slowly to the solution at 0~5° C. and the mixture was stirred at 5° C. for 2 hours. And then, pyridine (0.65 ml) and 2-amino-2-methyl-1-propanol (0.4 g) were added in order, the solution was stirred at 0~5° C. for 2 hours and heated to 20° C. and stirred for 1 hour. The reaction mixture was washed with water twice and dried over anhydrous magnesium sulfate. Then, the solvent was concentrated under reduced pressure. The concentrated residue was crystallized by treatment with ether and further recrystallized using ethyl acetate and ether. The recrystallized product was filtered and dried to give 1.5 g (yield: 84%) of a desired compound.

m.p.: 113~115° C.; $^1$H-NMR(CDCl$_3$), ppm: δ 1.22(d, 6H), 1.41(s, 6H), 3.10(m, 4H), 3.52(m, 3H), 3.68(s, 2H), 3.90(m, 2H), 4.14(s, 1H), 6.31(s, 1H), 6.85(m, 1H), 6.96(m, 1H), 7.45(m, 2H), 7.67(m, 1H), 7.77(m, 2H)

EXAMPLE 31

1-[N-[(1S)-2-Hydroxy-1-methylethyl]carbamoyl]-4-[1-[3-(isopropylamino)-2-pyridyl]piperazin-4-yl-carbonyl]benzene 4-[1-[3-(Isopropylamino)-2-pyridyl]piperazin-4-yl-carbonyl]benzoic acid methyl ester (1.8 g) and (S)-(+)-2-amino-1-propanol (0.71 g) were dissolved in methanol (30 ml) and heated to reflux for 12 hours. The reaction mixture was cooled and with the slow addition of excess of water at 40° C. to precipitate the crystals, the mixture was cooled again and stirred at 20° C. for 1 hour. Following with filtration and washing with water, the filtered solid was recrystallized using isopropanol and ether, filtered and dried to give 1.66 g (yield: 83%) of the desired compound.

m.p. : 132~133° C.; $^1$H-NMR(CDCl$_3$), ppm: δ 1.21(d, 6H), 1.29(d, 3H), 3.05(m, 4H), 3.49(m, 3H), 3.63(m, 1H), 3.78(m, 1H), 3.89(m, 2H), 4.13(m, 1H), 4.25(m, 1H), 6.67 (m, 1H), 6.85(m, 1H), 6.95(m, 1H), 7.40(m, 2H), 7.66(m, 1H), 7.78(m, 2H)

EXAMPLE 32

1-[N-[(1R)-2-Hydroxy-1-methylethyl]carbamoyl]-4-[1-[3-(isopropylamino)-2-pyridyl]piperazin-4-yl-carbonyl]benzene The desired compound was obtained by the same synthetic method as described in the Example 31.

Yield: 75%; $^1$H-NMR(CDCl$_3$), ppm: δ 1.20(d, 6H), 1.29 (d, 3H), 3.05(m, 4H), 3.50(m, 3H), 3.63(m, 1H), 3.78(m, 1H), 3.90(m, 2H), 4.13(m, 1H), 4.24(m, 1H), 6.67(m, 1H), 6.86(m, 1H), 6.95(m, 1H), 7.40(m, 2H), 7.66(m, 1H), 7.79 (m, 2H)

EXAMPLE 33

1-[N-[(1S)-2-Hydroxy-1-(1-methylethyl)ethyl]carbamoyl]-4-[1-[3-(isopropylamino)-2-pyridyl]piperazin-4-yl-carbonyl]benzene By the same procedure as described in the example 30, synthesis was carried out starting with 4-[1-[3-(isopropylamino)-2-pyridyl]piperazin-4-yl-carbonyl] benzoic acid and using (S)-(+)-2-amino-3-methyl-1-butanol. Then, the product was recrystallized using ethanol and isopropyl ether to give a desired compound.

Yield: 80%; m.p.: 82~83° C. $^1$H-NMR(CDCl$_3$), ppm: δ 0.98(d, 6H), 1.21(d, 6H), 2.01(m, 1H), 3.08(m, 4H), 3.53(m, 3H), 3.82(m, 2H), 3.93(m, 3H), 4.14(m, 1H), 6.70(m, 1H), 6.85(m, 1H), 6.95(m, 1H), 7.39(m, 2H), 7.66(m, 1H), 7.77 (m, 2H)

EXAMPLE 34

1-[N-[(1R)-2-Hydroxy-1-(1-methylethyl)ethyl]carbamoyl]-4-[1-[3-(isopropylamino)-2-pyridyl]piperazin-4-yl-carbonyl]benzene The desired compound was obtained by the same synthetic method as described in the Example 33.

Yield: 72%; m.p.: 86~88° C. $^1$H-NMR(CDCl3), ppm: δ 0.99(d, 6H), 1.21(d, 6H), 2.02(m, 1H), 3.06(m, 4H), 3.51(m, 3H), 3.80(m, 2H), 3.92(m, 3H), 4.13(m, 1H), 6.68(m, 1H), 6.83(m, 1H), 6.96(m, 1H), 7.40(m, 2H), 7.65(m, 1H), 7.78 (m, 2H)

EXAMPLE 35

1-[N-[(1S)-1-Ethyl-2-hydroxyethyl]carbamoyl]-4-[1-[3-(isopropylamino)-2-pyridyl] piperazin-4-yl-carbonyl]benzene By the same procedure as described in the example 31, synthesis was carried out starting with 4-[1-[3-(isopropylamino)-2-pyridyl]piperazin4-yl-carbonyl]benzoic acid methyl ester and using (S)-(+)-2-amino-1-butanol. Then, the product was recrystallized using acetonitrile and isopropyl ether to give the desired compound.

Yield: 79%; $^1$H-NMR(CDCl$_3$), ppm: δ 0.97(t, 3H), 1.21 (d, 6H), 1.73(m, 1H), 1.85(m, 1H), 3.06(m, 4H), 3.51(m, 3H), 3.81(m, 2H), 3.92(m, 2H), 4.11(m, 2H), 6.69(m, 1H), 6.84(m, 1H), 6.97(m, 1H), 7.41(m, 2H), 7.65(m, 1H), 7.79 (m, 2H)

EXAMPLE 36

1-[N-[(1R)-1-Ethyl-2-hydroxyethyl]carbamoyl]-4-[1-[3-(isopropylamino)-2-pyridyl]piperazin-4-yl-carbonyl]benzene The desired compound was obtained by the same synthetic method as described in the Example 35.

Yield: 73%; $^1$H-NMR(CDCl$_3$), ppm: δ 0.98(t, 3H), 1.21 (d, 6H), 1.75(m, 1H), 1.84(m, 1H), 3.05(m, 4H), 3.51(m, 3H), 3.80(m, 2H), 3.93(m, 2H), 4.11(m, 2H), 6.69(m, 1H), 6.84(m, 1H), 6.98(m, 1H), 7.41(m, 2H), 7.65(m, 1H), 7.80 (m, 2H)

EXAMPLE 37

1-[N-(1-Ethyl-2-hydroxyethyl)carbamoyl]-4-[1-[3-(isopropylamino)-2-pyridyl]piperazin-4-yl-carbonyl] benzene The desired compound was obtained by the same synthetic method as described in the example 35.

Yield: 84%; $^1$H-NMR(CDCl$_3$), ppm: δ 0.98(t, 3H), 1.21 (d, 6H), 1.76(m, 1H), 1.84(m, 1H), 3.06(m, 4H), 3.51(m, 3H), 3.81(m, 2H), 3.92(m, 2H), 4.11(m, 2H), 6.69(m, 1H), 6.84(m, 1H), 6.97(m, 1H), 7.40(m, 2H), 7.66(m, 1H), 7.79 (m, 2H)

EXAMPLE 38

1-[N-[(1S)-1-(Cyclohexylmethyl)-2-hydroxyethyl] carbamoyl]-4-[1-[3-(isopropylamino)-2-pyridyl] piperazin-4-yl-carbonyl]benzene 4-[1-[3-(Isopropylamino)-2-pyridyl]piperazin-4-yl-carbonyl]benzoic acid (1.5 g) was dissolved in methylene chloride (60 ml) and then, triethylamine (0.7 ml) was added and cooled. Pivaloyl chloride (0.58 ml) was added slowly to the solution at 0~5° C. and the mixture was stirred at SoC for 2 hours. And then triethylamine (1.7 ml) and (S)-(+)-2-amino-3-cyclohexyl-1-propanol hydrochloride (0.87 g) were added in order, the solution was stirred at 0° C. for 3 hours and heated slowly to 20° C. and stirred for 1 hour. The reaction mixture was washed with water twice and the solvent was concentrated under reduced pressure. The concentrated residue was recrystallized using isopropanol and ether. The recrystallized product was filtered and dried to give 2.07 g (yield: 80%) of the desired compound. m.p.: 139~140° C.; $^1$H-NMR(CDCl$_3$), ppm: δ 0.89~1.01(m, 2H), 1.22(m, 9H), 1.34(m, 1H), 1.45(m, 2H), 1.71(m, 4H), 1.81 (m, 1H), 3.10(m, 4H), 3.51(m, 3H), 3.61(m, 1H), 3.76(m, 1H), 3.89(m, 2H), 4.13(m, 1H), 4.26(m, 1H), 6.59(m, 1H), 6.83(m, 1H), 6.95(m, 1H), 7.40(m, 2H), 7.67(m, 1H), 7.77 (m, 2H)

EXAMPLE 39

1-[N-[(1S)-2-Hydroxy-1-phenylethyl]carbamoyl]-4-[1-[3-(isopropylamino)-2-pyridyl]piperazin-4-yl-carbonyl]benzene By the same procedure as described in the example 30, synthesis was carried out starting with 4-[1-[3-(isopropylamino)-2-pyridyl]piperazin-4-yl-carbonyl] benzoic acid and using (S)-(+)-2-amino-2-phenylethanol. Then, the product was recrystallized using ethanol and petroleum ether to give the desired compound.

Yield: 77%; m.p.: 93~95° C.; $^1$H-NMR(CDCl$_3$), ppm: δ 1.21(d, 6H), 3.10(m, 4H), 3.51(m, 3H), 3.88(m, 2H), 3.96 (m, 2H), 4.14(m, 1H), 5.20(m, 1H), 6.84(m, 1H), 6.94(m, 1H), 7.31~7.39(m, 8H), 7.65(m, 1H), 7.80(m, 2H)

EXAMPLE 40

1-[N-[(1R)-2-Hydroxy-1-phenylethyl]carbamoyl]-4-[1-[3-(isopropylamino)-2-pyridyl]piperazin-4-yl-carbonyl]benzene The desired compound was obtained by the same synthetic method as described in the Example 39.

Yield: 75%; $^1$H-NMR(CDCl$_3$), ppm: δ 1.20(d, 6H), 3.09 (m, 4H), 3.50(m, 3H), 3.88(m, 2H), 3.96(m, 2H), 4.13(m, 1H), 5.20(m, 1H), 6.84(m, 1H), 6.95(m, 1H), 7.30~7.39(m, 8H), 7.65(m, 1H), 7.80(m, 1H)

EXAMPLE 41

1-[N-[Bis(hydroxymethyl)methyl]carbamoyl]-4-[1-[3-(isopropylamino)-2-pyridyl]piperazin-4-yl-carbonyl]benzene By the same procedure as described in the example 31, synthesis was carried out starting with 4-[1-[3-(isopropylamino)-2-pyridyl]piperazin-4-yl-carbonyl] benzoic acid methyl ester and using 2-amino-1,3-propanediol. Then, the product was recrystallized using ethyl acetate and ether to give the desired compound.

Yield: 79%; m.p.: 147~149° C.; $^1$H-NMR(CDCl$_3$), ppm: δ 1.21(d, 6H), 3.06(m, 4H), 3.49(m, 3H), 3.90(m, 6H), 4.11(m, 1H), 6.85(m, 1H), 6.96(m, 1H), 7.38(m, 3H), 7.65 (m, 1H), 7.80(m, 2H)

EXAMPLE 42

1-[N-[1,1-Bis(hydroxymethyl)propyl]carbamoyl]-4-[1-[3-(isopropylamino)-2-pyridyl]piperazin-4-yl-carbonyl]benzene The desired compound was obtained by the same synthetic method as described in the Example 41.

Yield: 82%; $^1$H-NMR(CDCl$_3$), ppm: δ 0.99(t, 3H), 1.21 (d, 6H), 1.91(m, 2H), 3.06(m, 4H) 3.50(m, 3H), 3.90(m, 6H), 4.11(m, 1H), 6.86(m, 1H), 6.95(m, 1H), 7.38(m, 3H), 7.66(m, 1H), 7.80(m, 2H)

EXAMPLE 43

1-[N-[(2S)-2-Hydroxypropyl]carbamoyl]-4-[1-[3-(isopropylamino)-2-pyridyl]piperazin-4-yl-carbonyl] benzene By the same procedure as described in the example 31, synthesis was carried out starting with 4-[1-[3-(isopropylamino)-2-pyridyl]piperazin-4-yl-carbonyl] benzoic acid methyl ester and using (S)-(+)-1-amino-2-propanol. Then, the product was recrystallized using isopropanol and tetrahydrofuran to give the desired compound.

Yield: 81%; m.p.: 135° C.; $^1$H-NMR(CDCl$_3$), ppm: δ 1.21(m, 6H), 1.29(d, 3H), 3.05(m, 4H), 3.50(m, 3H), 3.59 (m, 1H), 3.72(m, 2H), 3.90(m, 2H), 4.13(m, 1H), 4.25(m, 1H), 6.67(m, 1H), 6.85(m, 1H), 6.95(m, 1H), 7.40(m, 2H), 7.66(m, 1H), 7.78(m, 2H)

EXAMPLE 44

1-[N-[(2R)-2-Hydroxypropyl]carbamoyl]-4-[1-[3-(isopropylamino)- 2-pyridyl]piperazin-4-yl-carbonyl]benzene The desired compound was obtained by the same synthetic method as described in the Example 43.

Yield: 74%; m.p.: 133~134° C.; $^1$H-NMR(CDCl$_3$), ppm: δ 1.20(m, 6H), 1.29(d, 3H), 3.04(m, 4H), 3.50(m, 3H), 3.60(m, 1H), 3.73(m, 2H), 3.91(m, 2H), 4.11(m, 1H), 4.25 (m, 1H), 6.67(m, 1H), 6.85(m, 1H), 6.95(m, 1H), 7.40(m, 2H), 7.66(m, 1H), 7.78(m, 2H)

EXAMPLE 45

4-[1-[3-(isopropylamino)-2-pyridyl]piperazin-4-yl-carbonyl]-1-[N-(2-methoxyethyl)carbamoyl]benzene 4-[1-[3-(Isopropylamino)-2-pyridyl]piperazin-4-yl-carbonyl]benzoic acid methyl ester (1.6 g) was dissolved in methanol (35 ml) and then, 2-methoxyethylamine (0.68 g) was added. And then, the reaction mixture was heated to reflux for 10 hours. The mixture was cooled, and after excess of water was added slowly to the solution at 35~40° C. to precipitate the crystals, the solution was slowly cooled again, stirred at 10° C. for 1 hour and filtered. The filtered solid was washed with a co-solvent (water:methanol=4:1, v/v) and was recrystallized using isopropanol and ether, filtered and dried to give 1.39 g (yield: 78%) of the desired compound. m.p.: 120~121° C.; $^1$H-NMR(CDCl$_3$), ppm: δ 1.23(d, 6H), 3.15(m, 4H), 3.38(s, 3H), 3.55(m, 5H), 3.64(m, 2H), 3.91(m, 2H), 6.55(m, 1H), 6.90(m, 1H), 6.99(m, 1H), 7.49(m, 2H), 7.70(m, 1H), 7.81(m, 2H)

EXAMPLE 46

1-[N,N-Bis(2-methoxyethyl)carbamoyl]-4-[1-[3-(isopropylamino)-2-pyridyl]piperazin-4-yl-carbonyl] benzene 4-[1-[3-(Isopropylamino)-2-pyridyl]piperazin-4-yl-carbonyl]benzoic acid (1.5 g) was dissolved in methylene chloride (45 ml) and then, triethylamine (0.7 ml) was added and cooled. Pivaloyl chloride (0.58 ml) was added slowly to the solution at 0~5° C. and the mixture was stirred at 5° C. for 2 hours. N,N-Diisopropylethylamine (0.8 ml) and bis(2-methoxyethyl)amine (0.6 g) were added in order, the solution was stirred at 0~5° C. for 2 hours and heated slowly to 20~25° C. and stirred for 30 minutes. The reaction mixture was washed with water twice and with aqueous 5% sodium bicarbonate. Then, the solvent was dried over anhydrous sodium sulfate and the solvent was concentrated under reduced pressure. The concentrated residue was crystallized by treatment with ether and further recrystallized using ethyl acetate and ether. The recrystallized product was filtered and dried to give 1.65 g (yield: 84%) of the desired compound. m.p.: 82~83° C.; $^1$H-NMR(CDCl$_3$), ppm: δ 1.21(d, 6H), 3.08(m, 4H), 3.25(s, 3H), 3.36(m, 5H), 3.52(m, 5H), 3.64(m, 2H), 3.74(m, 2H), 3.90(m, 2H), 4.15(m, 1H), 6.82(m, 1H), 6.91(m, 1H), 7.44(m, 4H), 7.66(m, 1H)

EXAMPLE 47

4-[1-[3-(Isopropylamino)-2-pyridyl]piperazin-4-yl-carbonyl]-1-[N-(3-methoxypropyl)carbamoyl]benzene The desired compound was obtained by the same synthetic method as described in the Example 45.

Yield: 75%; $^1$H-NMR(CDCl$_3$), ppm: δ 1.22(d, 6H), 1.80 (m, 3H), 3.13(m, 4H), 3.39(s, 3H), 3.53(m, 5H), 3.63(m, 2H), 3.91(m, 2H), 6.55(m, 1H), 6.90(m, 1H), 6.96(m, 1H), 7.49(m, 2H), 7.71(m, 1H), 7.80(m, 2H)

EXAMPLE 48

1-[N-(2,2-Dimethoxyethyl)-N-methylcarbamoyl]-4-[1-[3-(isopropylamino)-2-pyridyl]piperazin-4-yl-carbonyl]benzene By the same procedure as described in the example 46, synthesis was carried out starting with 4-[1-[3-(isopropylamino)-2-pyridyl]piperazin-4-yl-carbonyl]benzoic acid and using methylaminoacetaldehyde dimethyl acetal. Then, the product was recrystallized using acetonitrile and ether to give the desired compound.

Yield: 80%; $^1$H-NMR(CDCl$_3$), ppm: δ 1.21(d, 6H), 3.01 (s, 3H), 3.14(m, 4H), 3.38(s, 3H), 3.41(s, 3H), 3.51(m, 5H), 3.91(m, 2H), 4.82(m, 1H), 6.87(m, 1H), 6.94(m, 1H), 7.46 (m, 4H), 7.67(m, 1H)

EXAMPLE 49

1-[N-(2,2-Diethoxyethyl)carbamoyl]-4-[1-[3-(isopropylamino)-2-pyridyl]piperazin-4-yl-carbonyl]benzene By the same procedure as described in the example 46, synthesis was carried out starting with 4-[1-[3-(isopropylamino)-2-pyridyl]piperazin-4-yl-carbonyl]benzoic acid and using 2,2-diethoxyethylamine. Then, the product was recrystallized using ethanol and isopropyl ether to give the desired compound.

Yield: 76%; $^1$H-NMR(CDCl$_3$), ppm: δ 1.22(m, 12H), 3.15(m, 4H), 3.50(m, 5H), 3.57(m, 2H), 3.80(m, 2H), 3.92 (m, 2H), 4.85(m, 1H), 6.87(m, 1H), 6.93(m, 1H), 7.45(m, 4H), 7.67(m, 1H)

EXAMPLE 50

1-[N-[(1,3-Dioxolan-2-yl)methyl]-N-methylcarbamoyl]-4-[1-[3-(isopropylamino)-2-pyridyl]piperazin-4-yl-carbonyl]benzene The desired compound was obtained by the same synthetic method as described in the Example 46.

Yield: 81%; m.p.: 102~104° C.; $^1$H-NMR(CDCl$_3$), ppm: δ 1.22(d, 6H), 3.12(m, 7H), 3.42(m, 1H), 3.54(m, 3H), 3.72(m, 1H), 3.90(m, 6H), 4.15(m, 1H), 5.01(m, 1H), 6.87 (m, 2H), 7.46(m, 4H), 7.69(m, 1H)

EXAMPLE 51

4-[1-[3-(Isopropylamino)-2-pyridyl]piperazin-4-yl-carbonyl]-1-[N-[(tetrahydrofuran-2-yl)niethyl]carbamoyl]benzene By the same procedure as described in the example 45, synthesis was carried out starting with 4-[1-[3-(isopropylamino)-2-pyridyl]piperazin-4-yl-carbonyl]benzoic acid methyl ester and using tetrahydrofurfurylamine. Then, the product was recrystallized using ethyl acetate and hexane to give the desired compound.

Yield: 83%; m.p.: 146~147° C.; $^1$H-NMR(CDCl$_3$), ppm: δ 1.21(d, 6H), 1.61(m, 1H), 1.94(m, 2H), 2.02(m, 1H), 3.11(m, 4H), 3.33(m, 1H), 3.52(m, 3H), 3.76(m, 2H), 3.86 (m, 3H), 4.05(m, 1H), 4.12(m, 1H), 6.53(m, 1H), 6.87(m, 1H), 6.95(m, 1H), 7.49(m, 2H), 7.68(m, 1H), 7.81(m, 2H)

EXAMPLE 52

4-[1-[3-(Isopropylamino)-2-pyridyl]piperazin-4-yl-carbonyl]-1-[N-[[(2R)-tetrahydrofuran-2-yl]methyl]carbamoyl]benzene The desired compound was obtained by the same synthetic method as described in the Example 51.

Yield: 77%; $^1$H-NMR(CDCl$_3$), ppm: δ 1.22(d, 6H), 1.60 (m, 1H), 1.93(m, 2H), 2.02(m, 1H), 3.11(m, 4H), 3.31(m, 1H), 3.51(m, 3H), 3.77(m, 2H), 3.86(m, 3H), 4.06(m, 1H), 4.13(m, 1H), 6.52(m, 1H), 6.87(m, 1H), 6.95(m, 1H), 7.50 (m, 2H), 7.68(m, 1H), 7.82(m, 2H)

EXAMPLE 53

4-[1-[3-(Isopropylamino)-2-pyridyl]piperazin-4-yl-carbonyl]-1-[N-[[(2S)-tetrahydrofuran-2-yl]methyl]carbamoyl]benzene The desired compound was obtained by the same synthetic method as described in the Example 51.

Yield: 79%; $^1$H-NMR(CDCl$_3$), ppm: δ 1.21(d, 6H), 1.61 (m, 1H), 1.93(m, 2H), 2.03(m, 1H), 3.12(m, 4H), 3.32(m, 1H), 3.52(m, 3H), 3.77(m, 2H), 3.86(m, 3H), 4.06(m, 1H), 4.12(m, 1H), 6.53(m, 1H), 6.87(m, 1H), 6.94(m, 1H), 7.49 (m, 2H), 7.68(m, 1H), 7.81(m, 2H)

EXAMPLE 54

4-[1-[3-(Isopropylamino)-2-pyridyl]piperazin-4-yl-carbonyl]-1-(morpholin-4-yl-carbonyl)benzene 4-[1-[3-(Isopropylamino)-2-pyridyl]piperazin-4-yl-carbonyl]benzoic acid (1.5 g) was dissolved in methylene chloride (45 ml) and then, triethylamine (0.7 ml) was added and cooled. Pivaloyl chloride (0.58 ml) was added slowly to the solution at 0~5° C. and the mixture was stirred at 5° C. for 2 hours.

After the slow addition of morpholine (0.91 g), the solution was stirred at 0~5° C. for 3 hours. The reaction mixture was washed with water twice and with aqueous 1% acetic acid and 5% sodium bicarbonate one time each. Then, the solvent was dried over anhydrous sodium sulfate and the solvent was concentrated under reduced pressure. The concentrated residue was crystallized by treatment with ether and further recrystallized using methanol and hexane. The recrystallized product was filtered and dried to give 1.52 g (yield: 85%) of the desired compound. m.p.: 139° C.; $^1$H-NMR(CDCl$_3$), ppm: δ 1.23(d, 6H), 3.10(m, 4H), 3.41(m, 2H), 3.53(m, 5H), 3.77(m, 4H), 3.90(m, 2H), 4.14(m, 1H), 6.85(m, 1H), 6.96(m, 1H), 7.48(m, 4H), 7.67(m, 1H)

EXAMPLE 55

4-[1-[3-(Isopropylamino)-2-pyridyl]piperazin-4-yl-carbonyl]-1-(thiomorpholin-4-yl-carbonyl)benzene The desired compound was obtained by the same synthetic method as described in the Example 54.

Yield: 76%; m.p.: 163~164° C.; $^1$H-NMR(CDCl$_3$), ppm: δ 1.21(d, 6H), 2.53(m, 2H), 2.72(m, 2H), 3.10(m, 4H), 3.52(m, 3H), 3.63(m, 2H), 3.91(m, 2H), 4.01(m, 2H), 4.14 (m, 1H), 6.85(m, 1H), 6.93(m, 1H), 7.41(m, 2H), 7.46(m, 2H), 7.67(m, 1H)

EXAMPLE 56

4-[1-[3-(Isopropylamino)-2-pyridyl]piperazin-4-yl-carbonyl]-1-[N-[2-(morpholin-4-yl)ethyl]carbamoyl]benzene 4-[1-[3-(Isopropylamino)-2-pyridyl]piperazin-4-yl-carbonyl]benzoic acid methyl ester (1.2 g) was dissolved in a co-solvent of ethanol (10 ml) and acetonitrile (20 ml), and 4-(2-aminoethyl)morpholine (0.82 g) was added. The reaction mixture was heated to reflux for 15 hours and cooled. After excess of water was added to the solution at 30° C. to precipitate the crystals, the solution was stirred for 1 hour. Then, the solution was again cooled slowly, stirred at 10~15° C. for 2 hours and filtered. The filtered crystal was washed with preheated water(40° C.) and was recrystallized using isopropanol and ether, filtered and dried to give 1.22 g (yield: 81%) of the desired compound.

m.p.: 114~116° C.; $^1$H-NMR(CDCl$_3$), ppm: δ 1.22(d, 6H), 2.59(m, 4H), 2.68(m, 2H), 3.04(m, 4H), 3.57(m, 5H), 3.77(m, 4H), 3.90(m, 2H), 4.12(m, 1H), 6.81(m, 1H), 6.92 (m, 1H), 7.10(m, 1H), 7.48(m, 2H), 7.65(m, 1H), 7.85(m, 2H)

EXAMPLE 57

4-[1-[3-(Isopropylamino)-2-pyridyl]piperazin-4-yl-carbonyl]-1-[N-[3-(morpholin-4-yl)propyl]carbamoyl]benzene The desired compound was obtained by the same synthetic method as described in the Example 56.

Yield: 74%; m.p.: 103° C.; $^1$H-NMR(CDCl$_3$), ppm: δ 1.21(d, 6H), 1.85(m, 2H), 2.62(m, 6H), 3.05(m, 4H), 3.53 (m, 5H), 3.75(m, 4H), 3.91(m, 2H), 4.12(m, 1H), 6.81(m, 1H), 6.92(m, 1H), 7.51(m, 2H), 7.66(m, 1H), 7.87(m, 2H), 8.13(m, 1H)

EXAMPLE 58

4-[1-[3-(Isopropylamino)-2-pyridyl]piperazin4-yl-carbonyl]-1-[N-[2-(piperidin-1-yl)ethyl]carbamoyl]benzene By the same procedure as described in the example 56, synthesis was carried out starting with 4-[1-[3-(isopropylamino)-2-pyridyl]piperazin-4-yl-carbonyl]benzoic acid methyl ester and using 1-(2-aminoethyl)piperidine. Then, the product was recrystallized using acetonitrile and hexane to give the desired compound.

Yield: 70%; m.p.: 106~107° C.; $^1$H-NMR(CDCl$_3$), ppm: δ 1.22(d, 6H), 1.46(m, 2H), 1.61(m, 4H), 2.47(m, 4H), 2.58(m, 2H), 3.06(m, 4H), 3.54(m, 5H), 3.90(m, 2H), 4.12 (m, 1H), 6.81(m, 1H), 6.91(m, 1H), 7.14(m, 1H), 7.48(m, 2H), 7.66(m, 1H), 7.83(m, 2H)

EXAMPLE 59

1-[N-[2-(Dimethylamino)ethyl]carbamoyl]-4-[1-[3-(isopropylamino)-2-pyridyl]piperazin-4-yl-carbonyl]benzene By the same procedure as described in the example 45, synthesis was carried out starting with 4-[1-[3-(isopropylamino)-2-pyridyl]piperazin-4-yl-carbonyl]benzoic acid methyl ester and using N,N-dimethylethylenediamine. Then, the product was recrystallized using ethanol and isopropyl ether to give the desired compound.

Yield: 79%; m.p.: 133° C.; $^1$H-NMR(CDCl$_3$), ppm: δ 1.22(d, 6H), 2.31(s, 6H), 2.57(m, 2H), 3.09(m, 4H), 3.53(m, 5H), 3.91(m, 2H), 4.13(m, 1H), 6.80(m, 1H), 6.91(m, 1H), 7.04(m, 1H), 7.48(m, 2H), 7.66(m, 1H), 7.86(m, 2H)

EXAMPLE 60

1-[N-[2-(Dimethylamino)ethyl]-N-methylcarbamoyl]-4-[1-[3-(isopropylamino)-2-pyridyl]piperazin-4-yl-carbonyl]benzene By the same procedure as described in the example 46, synthesis was carried out starting with 4-[1-[3-(isopropylamino)-2-pyridyl]piperazin-4-yl-carbonyl]benzoic acid and using N,N,N'-trimethylethylenediamine. Then, the product was recrystallized using isopropanol and ether to give the desired compound.

Yield: 80%; $^1$H-NMR(CDCl$_3$), ppm: (1.22(d, 6H), 2.31(s, 6H), 2.58(m, 2H), 3.01(s, 3H), 3.10(m, 4H), 3.53(m, 5H), 3.90(m, 2H), 4.12(m, 1H), 6.80(m, 1H), 6.92(m, 1H), 7.48 (m, 2H), 7.67(m, 1H), 7.86(m, 2H)

EXAMPLE 61

1-[N-[2-(Dimethylamino)ethyl]-N-ethylcarbamoyl]-4-[1-[3-(isopropylamino)-2-pyridyl]piperazin-4-yl-carbonyl]benzene The desired compound was obtained by the same synthetic method as described in the Example 60.

Yield: 74%; $^1$H-NMR(CDCl$_3$), ppm: δ 1.10(t, 3H), 1.22 (d, 6H), 2.30(s, 6H), 2.59(m, 2H), 3.11(m, 4H), 3.52(m, 7H), 3.91(m, 2H), 4.12(m, 1H), 6.81(m, 1H), 6.92(m, 1H), 7.49 (m, 2H), 7.67(m, 1H), 7.87(m, 2H)

EXAMPLE 62

1-[N-[2-(Diethylamino)ethyl]carbamoyl]-4-[1-[3-(isopropylamino)-2-pyridyl]piperazin-4-yl-carbonyl]benzene By the same procedure as described in the example 45, synthesis was carried out starting with 4-[1-[3-(isopropylamino)-2-pyridyl]piperazin-4-yl-carbonyl]benzoic acid methyl ester and using N,N-diethylethylenediamine. Then, the product was recrystallized using isopropanol and hexane to give the desired compound.

Yield: 76%; $^1$H-NMR(CDCl$_3$), ppm: δ 1.02(t, 6H), 1.22 (d, 6H), 2.60(m, 6H), 3.11(m, 4H), 3.51(m, 5H), 3.90(m, 2H), 4.13(m, 1H), 6.18(m, 1H), 6.92(m, 1H), 7.05(m, 1H), 7.49(m, 2H), 7.67(m, 1H), 7.87(m, 2H)

Hereinafter, the anti-HBV activity of terephthalamide derivatives of the above formula 1 according to the present invention was evaluated in vitro. The evaluation procedure and results were described in the following Experiments 1 to 4.

Experiment 1: The inhibitory activity against HBV polymerase in vitro.

Recently, the inventors of the present invention have produced a recombinant HBV polymerase that is expressed from *E.coli* transformant, measured its enzyme activity and filed patent applications thereof [Korean Patent Application Nos. 94-3918, 96-33998 and 96-63255].

The inventions have established a method of measuring the reverse transcriptase activity of HBV polymerase in vitro. The fundamental principle is the same as the ELISA method, and after reacting the substrate with biotin- and DIG-modified nucleotide, a method of recognizing the polymerized substrate as anti-DIG antibody with peroxidase was used. 200, of HBV polymerase, 200, of reaction mixture and 20 μ of test compound were mixed and reacted at 14~30° C. for 18~24 hours. Then, the inhibitory effect of test compound against reverse trascriptase activity in the HBV polymerase was examined, compared with the results of control tests without the test compound. The inhibitory activity of each test compound is shown in the following Table 1.

TABLE 1

The inhibitory effects of reverse transcriptase (RT) enzyme activity of hepatitis B virus (HBV)

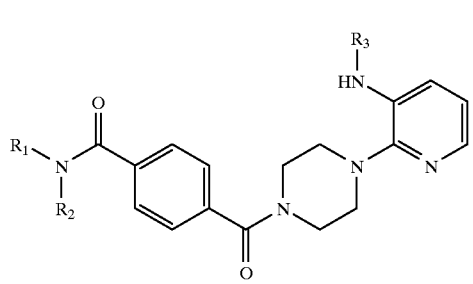

(1)

| Compounds | $R_1R_2N-$ | $R_3$ | Inhibitory effect of HBV-RT (%) 1 μg/ml | Inhibitory effect of HBV-RT (%) 0.1 μg/ml |
|---|---|---|---|---|
| Compound No. 1 | HOCH$_2$CH$_2$(H)N— | (CH$_3$)$_2$CH— | 55 | 53 |
| Compound No. 2 | HOCH$_2$CH$_2$CH$_2$(H)N— | " | 42 | 34 |
| Compound No. 5 | HOCH$_2$CH$_2$(CH$_3$)N— | " | 48 | 40 |
| Compound No. 6 | HOCH$_2$CH$_2$(CH$_3$CH$_2$)N— | " | 51 | 30 |
| Compound No. 11 | HOCH$_2$CH$_2$(C$_6$H$_5$)N— | " | 76 | 20 |
| Compound No. 12 | HOCH$_2$CH$_2$(HOCH$_2$CH$_2$)N— | " | 63 | 52 |

TABLE 1-continued

The inhibitory effects of reverse transcriptase (RT) enzyme activity of hepatitis B virus (HBV)

(1)

| Compounds | $\begin{array}{c}R_1\\ \diagdown N-\\ R_2\end{array}$ | $R_3$ | Inhibitory effect of HBV-RT (%) | |
|---|---|---|---|---|
| | | | 1 μg/ml | 0.1 μg/ml |
| Compound No. 13 | (CH₃CH₂)₂N— | " | 70 | 55 |
| Compound No. 16 | (HOCH(CH₃)CH₂)₂N— | (CH₃)₂CH— | 78 | 45 |
| Compound No. 18 | HOCH₂CH₂(CH₃CH₂)N— | CH₃CH₂— | 63 | 28 |
| Compound No. 20 | CH₃—N(piperazine)N— | (CH₃)₂CH— | 58 | 43 |
| Compound No. 26 | HOCH₂CH₂—N(piperazine)N— | " | 54 | 32 |
| Compound No. 31 | HOCH₂CH(OH)CH₂—N(piperazine)N— | " | 52 | 30 |
| Compound No. 32 | HOCH₂CH₂OCH₂CH₂—N(piperazine)N— | " | 71 | 40 |
| Compound No. 33 | HOCH₂CH₂—N(piperazine)N— | CH₃CH₂— | 69 | 37 |
| Compound No. 34 | HOCH₂C(CH₃)₂—NH— | (CH₃)₂CH— | 53 | 41 |

TABLE 1-continued

The inhibitory effects of reverse transcriptase (RT) enzyme activity of hepatitis B virus (HBV)

$$\text{Structure (1): } R_1R_2N-C(O)-C_6H_4-C(O)-N(\text{piperazine})N-\text{pyridine}-NHR_3$$

| Compounds | $\begin{array}{c} R_1 \\ | \\ R_2-N- \end{array}$ | $R_3$ | Inhibitory effect of HBV-RT (%) 1 μg/ml | 0.1 μg/ml |
|---|---|---|---|---|
| Compound No. 35 | HOCH$_2$CH(CH$_3$)—NH— , (S) | " | 82 | 62 |
| Compound No. 38 | HOCH$_2$CH(CH(CH$_3$)$_2$)—NH— , (S) | (CH$_3$)$_2$CH— | 67 | 50 |
| Compound No. 39 | HOCH$_2$CH(CH(CH$_3$)$_2$)—NH— , (R) | " | 78 | 30 |
| Compound No. 48 | HOCH$_2$CH(C$_6$H$_5$)—NH— , (S) | " | 80 | 61 |
| Compound No. 52 | (HOCH$_2$)$_2$CH—NH— | " | 63 | 52 |
| Compound No. 56 | HOCH$_2$CH(CH$_3$)—NH—, (S) | " | 76 | 58 |
| Compound No. 61 | CH$_3$OCH$_2$CH$_2$—NH— | " | 81 | 33 |
| Compound No. 62 | (CH$_3$OCH$_2$CH$_2$)$_2$N— | " | 60 | 53 |
| Compound No. 71 | 1,3-dioxolan-2-yl-CH$_2$—N(CH$_3$)— | " | 51 | 35 |

TABLE 1-continued

The inhibitory effects of reverse transcriptase (RT) enzyme activity of hepatitis B virus (HBV)

(1)

[Structure of compound (1): R₁R₂N-C(=O)-phenyl-C(=O)-N(piperazine)N-pyridyl-NH-R₃]

| Compounds | R₁R₂N— | R₃ | Inhibitory effect of HBV-RT (%) | |
|---|---|---|---|---|
| | | | 1 μg/ml | 0.1 μg/ml |
| Compound No. 72 | [tetrahydrofuran-2-yl-CH₂—NH—] | (CH₃)₂CH— | 63 | 51 |
| Compound No. 76 | [morpholino—] | " | 79 | 49 |
| Compound No. 79 | [morpholino—CH₂CH₂—NH—] | " | 72 | 65 |
| Compound No. 80 | [morpholino—(CH₂)₃—NH—] | " | 66 | 40 |
| Compound No. 83 | (CH₃)₂NCH₂CH₂—N— | " | 65 | 62 |

Experiment 2: The inhibitory effects against RNase H activity of HBV polymerase.

1) Expression of the RNase H domain derived from human HBV polymerase

E.coli NM 522 was transformed by the expression vector pMRH respectively and the transformants were cultured in LB medium at 37° C., overnight. These growing cultures were diluted 1:100, inoculated into a glucose rich medium and incubated until OD600 reached 0.5. Then IPTG (isopropylthiogalactoside) was added into the medium of which the fine concentration was 0.5 mM. The above growing cultures were incubated again at 20° C. for 16 hours and the RNase H domain was expressed.

The above cultured broth was centrifuged for 10 minutes at 3,000 rpm and the cell pellet was washed with 10 ml of TNE column buffer (10 mN Tris-Cl, pH 8.0, 200 mM NaCl, 1 mM EDTA), and resuspended in 10 ml of TNE column buffer. The cells were freezed and thawed 4 times repeatedly, and then disrupted by sonication for 10 seconds 3 times. The crude extract prepared in the above process was centrifuged for 30 minutes at 13,000 rpm, 4° C. and the supernatant was separated. The above process was repeated 2 times and then the supernatant passed the amylose resin. The resin was washed by using column buffer with 50 times of resin volume, and the RNase H domain was eluted by using buffer containing 10 mM maltose.

In addition, the RNase H domain produced from the expression vector pMRH was purified by using histidine tag affinity column, because RNase H has a histidine tag at the C-terminus. The resin (Ni-NTA, QIAGEN) used in the histidine tag affinity column was activated by using sonication buffer (50 mM sodium phosphate, pH 8.0, 300 mM sodium chloride) and 4~5 ml of the activated resin was charged in the glass tube whose diameter was about 1 cm. The protein sample obtained from above description passed the resin at the 0.1 ml/min flow rate and the column was washed by using washing buffer with the 100~200 times volume of protein sample (50 mM sodium phosphate, pH 6.0, 300 mM sodium chloride, 10% glycerol). The recombinant protein was eluted by washing the column with concentration gradient of 0.01~0.5 M imidazole.

As a result, the active RNase H domain was separated from the histidine tag affinity column at 30 mM concentration of imidazole. The purified RNase H domain was mixed with 50% glycerol for storage at −20° C. after the removal of imidazole from it and employed fol the screening of HBV inhibitors.

2) Preparation of the substrate of the RNase H enzyme

In order to identify the RNase H activity, RNA/DNA complex which can be used as a substrate of the RNase H enzyme was prepared by performing in vitro transcription with *E coli* M.

As discussed in the above, the compound(1) according to the present invention, and its pharmaceutically acceptable salts are effective as active ingredients of inhibiting the proliferation of various viruses including HBV and HIV in that without any cytotoxicity.

3) Screening of active inhibitors against RNase H

The RNase H activity was measured by using recombinant RNase H enzyme and radiolabled RNA/DNA hybrid. In order to measure the RNase H activity, 1 μg of RNase H enzyme and test compound were mixed with buffer solution containing 40 mM Tris-Cl (pH 8.0), 4 mM magnesium chloride, 40 mM potassium chloride and 2 mM DTT. The mixture was pretreated on ice for 10 minutes. After pretreatment is completed, RNA/DNA hybrid was added to incubate at 37° C. for 3 hours. After the reaction was stopped, 7.5 M ammonium acetate in a volume of 1/2 and ethanol in a 3-fold volume were added. The above reaction mixture was incubated at −20° C. for more than 2 hours and centrifuged for 15 minutes at 4° C., 13,000 rpm. The supernatant was obtained and the radioactive signal of supernatant was measured by scintillation counter.

As a control, water was added instead of test compound and the inhibitory activity was calculated to compare with the control, when the radioactivity intensity on each test compound, was obtained. The inhibitory activity of each test compound is shown in the following table 2.

TABLE 2

The inhibitory effects of RNase H enzyme activity of hepatitis B virus (HBV) polymerization enzyme.

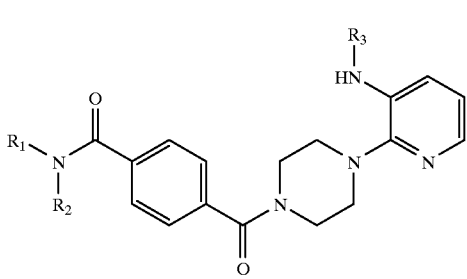

(1)

| Compound | $R_1R_2N-$ | $R_3$ | Inhibitory effect of HBV-RNase H (%) 1 μg/ml | 0.1 μg/ml |
|---|---|---|---|---|
| Compound No. 1 | HOCH$_2$CH$_2$-NH- | (CH$_3$)$_2$CH— | 80 | 11 |
| Compound No. 6 | HOCH$_2$CH$_2$(CH$_3$CH$_2$)N- | " | 83 | 55 |
| Compound No. 12 | (HOCH$_2$CH$_2$)$_2$N- | " | 91 | 86 |
| Compound No. 19 | piperazin-1-yl (HN piperazine) | " | 53 | 38 |
| Compound No. 26 | 4-(2-hydroxyethyl)piperazin-1-yl | " | 95 | 66 |

TABLE 2-continued

The inhibitory effects of RNase H enzyme activity of hepatitis B virus (HBV) polymerization enzyme.

(1)

[Structure of compound with $R_1$, $R_2$ on amide nitrogen, benzene ring, carbonyl-piperazine-pyridine with HN-$R_3$]

| Compound | $\begin{array}{c} R_1 \\ \diagdown \\ N- \\ \diagup \\ R_2 \end{array}$ | $R_3$ | Inhibitory effect of HBV-RNase H (%) | |
|---|---|---|---|---|
| | | | 1 µg/ml | 0.1 µg/ml |
| Compound No. 27 | HO(CH$_2$)$_3$—N⌒N— | | 81 | 73 |
| Compound No. 31 | HOCH$_2$CHCH$_2$—N⌒N— with OH on middle CH | " | 85 | 80 |
| Compound No. 52 | (HOCH$_2$)$_2$CH—N(H)— | (CH$_3$)$_2$CH— | 58 | 41 |
| Compound No. 71 | [1,3-dioxolan-2-yl]—CH$_2$—N(CH$_3$)— | " | 62 | 56 |

Experiment 3: The in vitro inhibition test against HIV reverse transcriptase

The inhibitory activity in vitro was measured using a non-radioactive reverse transcriptase assay Kit (Boehringer Mannheim).

At first, 20 µl(40 ng) HIV-RT was added to the wells coated with streptavidin and with the addition of 20 µl, reaction mixture containing template/primer hybrid poly(A)/oligo(dT)$_{15}$ and DIG-(digoxigenin)-dUTP, biotin-dUTP and TTP, 20 µl test compound was added and reacted at 37° C. for 1 hour. The control without test compound was used for the comparison of related activity. Since DNA containing nucleotide labeled with digoxigenin and biotine was prepared by the action of HIV-RT, it was combined with streptavidin coated at the bottom of the wells. After the reaction was completed, remaining impurities were removed by washing each well with 20 µl buffer solution (pH 7.0) for 30 seconds 5 times and with the addition of 200 µl anti-DIG-POD antibody, the mixture was reacted at 37° C. for 1 hour. For the removal of remaining impurities again, the reacting solution was washed with a buffer solution and with the addition of 200µl ABTS™ each, a substrate of POD (peroxidase), the solution was reacted at room temperature for 30 minutes. The absorbance was read by ELISA reader at 405 nm for the assay of reverse transcriptase activity and its inhibition activity.

The results of test compound are shown in the following table 3.

TABLE 3

The inhibitory effects against reverse transcriptase (HIV-RT) of AIDS virus

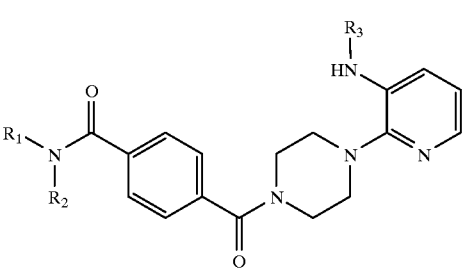

(1)

| Compound | $\underset{R_2}{\overset{R_1}{N}}-$ | $R_3$ | Inhibitory effect of HIV-RT (%) | |
|---|---|---|---|---|
| | | | 1 μg/ml | 0.1 μg/ml |
| Compound No. 1 | HOCH$_2$CH$_2$\N—<br>H/ | (CH$_3$)$_2$CH— | 62 | 41 |
| Compound No. 2 | HOCH$_2$CH$_2$CH$_2$\N—<br>H/ | " | 40 | 35 |
| Compound No. 5 | HOCH$_2$CH$_2$\N—<br>CH$_3$/ | " | 71 | 43 |
| Compound No. 7 | HOCH$_2$CH$_2$\N—<br>CH$_3$CH$_2$CH$_2$/ | " | 60 | 21 |
| Compound No. 11 | HOCH$_2$CH$_2$\N—<br>C$_6$H$_5$/ | " | 50 | 43 |
| Compound No. 12 | HOCH$_2$CH$_2$\N—<br>HOCH$_2$CH$_2$/ | " | 52 | 46 |
| Compound No. 14 | (CH$_3$)$_2$CH\N—<br>(CH$_3$)$_2$CH/ | " | 59 | 52 |
| Compound No. 16 | HOCH(CH$_3$)CH$_2$\N—<br>HOCH(CH$_3$)CH$_2$/ | (CH$_3$)$_2$CH— | 65 | 52 |
| Compound No. 17 | HOCH$_2$CH$_2$OCH$_2$CH$_2$—N—<br>H | " | 53 | 35 |
| Compound No. 19 | 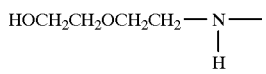 | " | 52 | 43 |

TABLE 3-continued

The inhibitory effects against reverse transcriptase (HIV-RT) of AIDS virus (1)

| Compound | $\begin{array}{c}R_1\\ \diagdown N—\\ R_2\end{array}$ | $R_3$ | Inhibitory effect of HIV-RT (%) | |
|---|---|---|---|---|
| | | | 1 μg/ml | 0.1 μg/ml |
| Compound No. 21 | $CH_3CH_2-N\bigcirc N-$ | " | 64 | 20 |
| Compound No. 26 | $HOCH_2CH_2-N\bigcirc N-$ | " | 55 | 45 |
| Compound No. 27 | $HO(CH_2)_3-N\bigcirc N-$ | " | 68 | 40 |
| Compound No. 32 | $HOCH_2CH_2OCH_2CH_2-N\bigcirc N-$ | " | 58 | 27 |
| Compound No. 34 | $\begin{array}{c}(CH_3)_2\\ HOCH_2C-N-\\ |\\ H\end{array}$ | " | 51 | 43 |
| Compound No. 38 | $\begin{array}{c}CH(CH_3)_2\\ |\\ HOCH_2CH-N-\\ |\\ H\quad,(S)\end{array}$ | " | 78 | 20 |
| Compound No. 39 | $\begin{array}{c}CH(CH_3)_2\\ |\\ HOCH_2CH-N-\\ |\\ H\quad,(R)\end{array}$ | $(CH_3)_2CH-$ | 75 | 25 |
| Compound No. 47 | $\begin{array}{c}CH_2-C_6H_{11}\\ |\\ HOCH_2CH-N-\\ |\\ H\quad,(S)\end{array}$ | " | 54 | 43 |

TABLE 3-continued

The inhibitory effects against reverse transcriptase (HIV-RT) of AIDS virus (1)

[Structure: R₁R₂N-C(=O)-C₆H₄-C(=O)-N(piperazine)N-pyridine-NHR₃]

| Compound | R₁R₂N— | R₃ | Inhibitory effect of HIV-RT (%) | |
|---|---|---|---|---|
| | | | 1 μg/ml | 0.1 μg/ml |
| Compound No. 48 | HOCH₂CH(C₆H₅)—NH— ,(S) | " | 51 | 46 |
| Compound No. 52 | (HOCH₂)₂CH—NH— | " | 61 | 57 |
| Compound No. 61 | CH₃OCH₂CH₂—NH— | " | 65 | 32 |
| Compound No. 62 | (CH₃OCH₂CH₂)₂N— | " | 58 | 41 |
| Compound No. 71 | (1,3-dioxolan-2-yl)CH₂—N(CH₃)— | " | 70 | 68 |
| Compound No. 76 | morpholino— | " | 52 | 43 |
| Compound No. 77 | thiomorpholino— | (CH₃)₂CH— | 40 | 28 |
| Compound No. 79 | morpholino-CH₂CH₂—NH— | " | 71 | 59 |
| Compound No. 80 | morpholino-(CH₂)₃—NH— | " | 56 | 43 |

TABLE 3-continued

The inhibitory effects against reverse transcriptase (HIV-RT) of AIDS virus

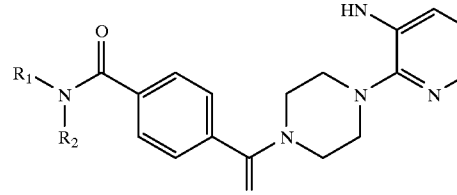

(1)

| Compound | $\begin{array}{c} R_1 \\ \diagdown N{-} \\ R_2 \end{array}$ | $R_3$ | Inhibitory effect of HIV-RT (%) | |
|---|---|---|---|---|
| | | | 1 µg/ml | 0.1 µg/ml |
| Compound No. 81 | 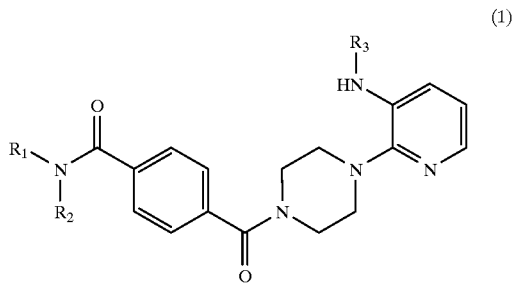 | " | 60 | 32 |
| Compound No. 83 | $(CH_3)_2NCH_2CH_2{-}N{-}$ | " | 65 | 62 |

Experiment 4: Cytotoxicity

The cytotoxicity test was carried out using HepG2 cells in vitro. As a result, terephthalamide derivatives of the above formula 1 according to the present invention, and its pharmaceutically acceptable salts proven not to have cytotoxicity with $CC_{50} \geqq 200$ µM. As discussed in the above, the compounds of the above formula 1 according to the present invention, and its pharmaceutically acceptable salts are effective as active ingredients of inhibiting the proliferation of various viruses including HBV and HIV in that without any cytotoxicity.

What is claimed is:

1. A terephthalamide derivative of the following formula 1:

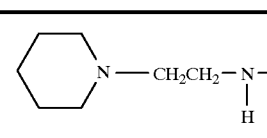

(1)

wherein:

$R_1$ and $R_2$ represent independently one selected from hydrogen atom; phenyl group; benzyl group; $C_1{\sim}C_6$ alkyl group; substituted $C_1{\sim}C_4$ alkyl group in which one substituent selected from di($C_1{\sim}C_4$ alkyl)amino, acetylamino group and heterocycles; $C_1{\sim}C_5$ hydroxyalkyl group; substituted $C_1{\sim}C_4$ hydroxyalkyl group in which one or two substituent selected from phenyl, benzyl, $C{\sim}C_4$ group and $C_1{\sim}C_7$ alkyl group; $C_2{\sim}C_6$ alkoxyalkyl group; di($C_2{\sim}C_6$ alkoxy)alkyl group; $C_2{\sim}C_5$ (hydroxyalkoxy)alkyl group; with the proviso that $R_1$ and $R_2$ do not simultaneously represent hydrogen atom;

further, $R_1$ and $R_2$ may be combined with one or two hetero atoms selected from nitrogen, oxygen and sulfur to form five or six membered heterocycles, wherein the heterocycles may be substituted with one substituent selected from $C_1{\sim}C_5$ alkyl, $C_3{\sim}C_6$ cycloalkyl, $C_3{\sim}C_5$ (hydroxyalkoxy)alkyl, $C_2{\sim}C_5$ hydroxyalkyl, $C_1{\sim}C_3$ alkyl-substituted $C_1{\sim}C_4$ hydroxyalkyl, $C_1{\sim}C_4$ dihydroxyalkyl and $C_1{\sim}C_3$ alkyl-substituted $C_1{\sim}C_4$ dihydroxyalkyl group;

$R_3$ represents $C_1{\sim}C_4$ alkyl group;

further, the above mentioned alkyl group includes straight or branched alkyl group or its pharmaceutically acceptable salt.

2. The terephthalamide derivative according to claim 1, wherein one between $R_1$ and $R_2$ is hydrogen atom and the other is $C_1{\sim}C_3$ alkoxy $C_1{\sim}C_4$ alkyl group; di($C_2{\sim}C_5$ alkoxy) $C_1{\sim}C_4$ alkyl group; 1,3-dioxolan-2-yl-methyl group; tetrahydrofuran-2-yl-methyl group; 2-(morpholin-4-yl)ethyl group; 3-(morpholin-4-yl)propyl group; 2-(piperidin-1-yl) ethyl group; di($C_1{\sim}C_3$ alkyl)amino $C_1{\sim}C_3$ alkyl group; 2-(acetylamino)ethyl group; 2-hydroxyethyl group; or substituted 2-hydroxyethyl group with one or two substituents selected from phenyl group, benzyl group, $C_1{\sim}C_3$ hydroxyalkyl group and $C_1{\sim}C_5$, alkyl group.

3. The terephthalamide derivative according to claim 1, wherein one between $R_1$ and $R_2$ is $C_1{\sim}C_3$ alkyl group and the other is di($C_1{\sim}C_3$ alkoxy) $C_2{\sim}C_3$ alkyl group; 1,3-dioxolan-2-yl-methyl group; tetrahydrofuran-2-yl-methyl group; 2-(morpholin-4-yl)ethyl group; 3-(morpholin-4-yl)propyl group; 2-(piperidin-1-yl)ethyl group; 2-hydroxyethyl group; di($C_1$~$C_3$ alkyl)amino $C_1$~$C_3$ alkyl group; or 2-(acetylamino)ethyl group.

4. The terephthalamide derivative according to claim 1, wherein said $R_1$ and $R_2$ are simultaneously $C_1$~$C_3$ alkyl group, hydroxyethyl, or 2-hydroxypropyl.

5. The terephthalamide derivative according to claim 1, wherein said $R_1$ and $R_2$ are combined with one or two hetero atoms selected from nitrogen, oxygen and sulfur to form a heterocycle selected from morpholine, thiomorpholine, pyrrolidine, piperidine and piperazine ring.

6. The terephthalamide derivative according to claim 5, wherein nitrogen atom at 4-position of said piperazine ring is substituted with hydrogen atom, $C_1$~$C_5$ alkyl group, $C_3$~$C_6$ cycloalkyl group, $C_2$~$C_5$ hydroxyalkyl group, $C_2$~$C_4$ dihydroxyalkyl group, $C_3$~$C_5$ (hydroxyalkoxy)alkyl group, $C_1$~$C_3$ alkyl-substituted $C_1$~$C_4$ hydroxyalkyl group, (2R)-3-hydroxy-2-methylpropyl group or (2S)-3-hydroxy-2-methylpropyl group.

7. A pharmaceutical composition containing terephthalamide derivative of the following formula 1, or its pharmaceutically acceptable salts as an active ingredient,

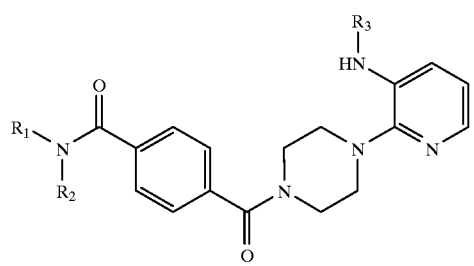

(1)

wherein $R_1$, $R_2$ and $R_3$ are the same as defined in claim 1, respectively.

8. An antiviral agent comprising terephthalamide derivative of the following formula 1, or its pharmaceutically acceptable salts as an active ingredient,

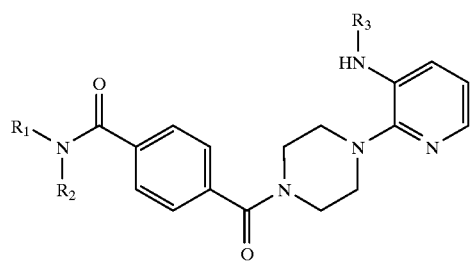

(1)

wherein $R_1$, $R_2$ and $R_3$ are the same as defined in claim 1, respectively.

9. The antiviral agent according to claim 8, wherein said virus represents hepatitis B virus(HBV) or human immunodeficiency virus (HIV).

10. A process for preparing terephthalamide derivatives of the following formula 1, comprising steps of reacting a compound of the following formula 2 and acid chloride to form an acid anhydride; and then reacting the intermediate with an amine compound of the following formula 3,

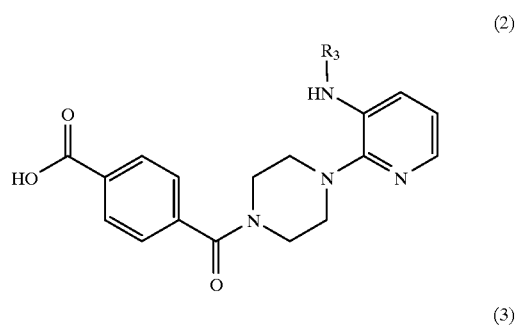

(2)

(3)

wherein: $R_1$, $R_2$ and $R_3$ are the same as defined in claim 1, respectively.

11. A process for preparing terephthalamide derivatives of the following formula 1, comprising nucleophilic substitution of a compound of the following formula 4 with an amine compound of the following formula 3, (3)

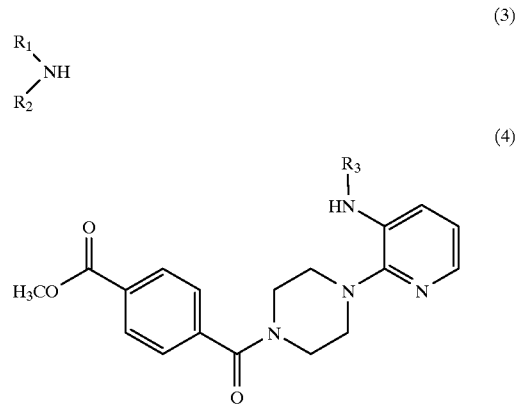

(4)

(1)

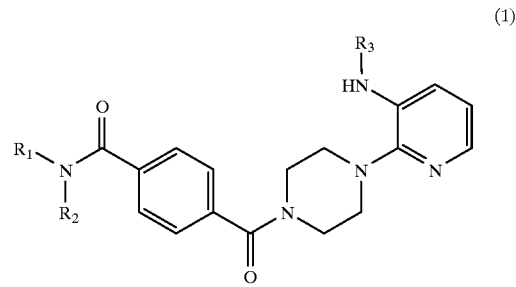

wherein: $R_1$, $R_2$ and $R_3$ are the same as defined in claim 1, respectively.

12. A process for preparing terephthalamide derivatives of the following formula 1b, comprising reaction of piperazine derivatives of the following formula 1a and halogen compound of the following formula 7 in the presence of tertiary organic base,

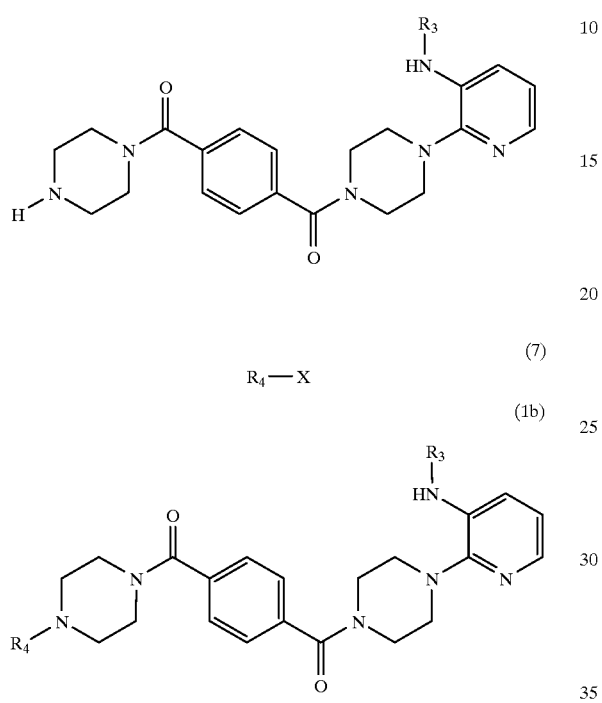

(1a)

$R_4$—X (7)

(1b)

wherein:
$R_3$ is the same as defined in claim 1;
$R_4$ represents hydrogen atom, $C_1$~$C_5$ alkyl group, $C_3$~$C_6$ cycloalkyl group, $C_2$~$C_5$ hydroxyalkyl group, $C_2$~$C_4$ dihydroxyalkyl group, $C_3$~$C_5$ (hydroxyalkoxy)alkyl group, or $C_1$~$C_3$ alkyl-substituted $C_2$~$C_4$ hydroxyalkyl group; and
X represents halogen atom.

13. A process for preparing terephthalamide derivative of the following formula 2, comprising steps of
reaction of mono-methyl terephthalate of the formula 9 and acid chloride to form an acid anhydride; then, the reaction mixture is further reacted with pyridylpiperazine derivative of the formula 8, to obtain terephthalic acid ester derivative including nitropyridyl group of the following formula 10;
reduction of the compound of the formula 10 to give the derivative of the formula 11 including aminopyridyl group;
reductive alkylation of the derivatives of the formula 11 with acetone or acetaldehyde in the presence of a selective reducing agent under acidic conditions to form terephthalic acid ester derivative of the formula 4; and
hydrolysis of terephthalic acid ester derivative of the formula 4,

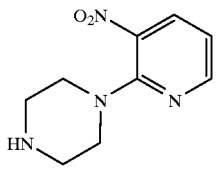

(8)

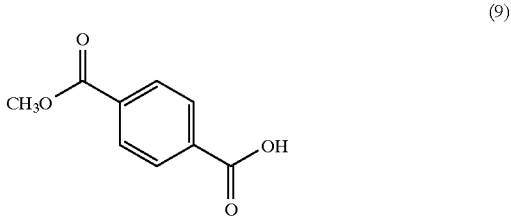

(9)

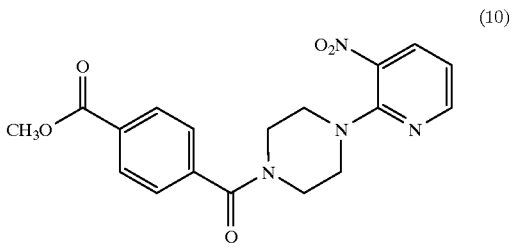

(10)

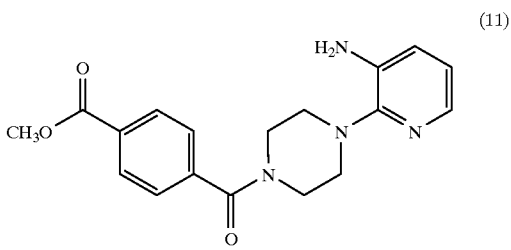

(11)

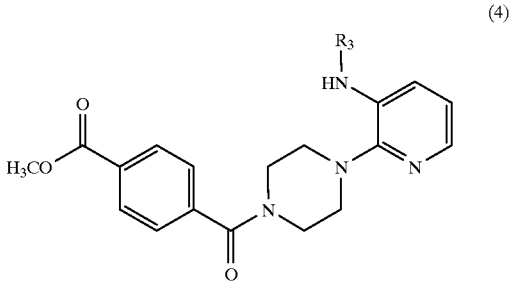

(4)

(2)

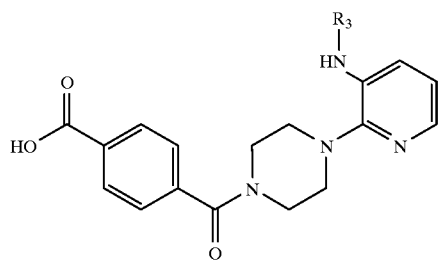

wherein $R_3$ is the same as defined in claim 1.

14. A terephthalamide derivative according to claim 1, wherein one $R_1$ or $R_2$ is hydrogen, and wherein the terephthalamide derivative has an (R)-type stereospecificity.

15. A terephthalamide derivative according to claim 1, wherein one of $R_1$ or $R_2$ is hydrogen, and wherein the terephthalamide derivative has an (S)-type stereospecificity.

* * * * *

UNITED STATES PATENT AND TRADEMARK OFFICE
CERTIFICATE OF CORRECTION

PATENT NO.: 5,922,871

DATED: July 13, 1999

INVENTOR(S): Yoon et al.

It is certified that an error appears in the above-identified patent and that said Letters Patent is hereby corrected as shown below:

CLAIM 1, Col. 50, L. 35 change "$C\sim C_4$" to --$C_1\sim C_4$ hydroxyalkyl--.

CLAIM 6, Col. 51, L. 19 italicize "*R*", and L. 20 italicize "*S*".

CLAIM 13, Col. 53, L. 47 italicize "*mono*".

Signed and Sealed this

Twenty-first Day of December, 1999

*Attest:*

Q. TODD DICKINSON

*Attesting Officer*     *Acting Commissioner of Patents and Trademarks*